United States Patent [19]
Janda et al.

[11] Patent Number: 5,827,827
[45] Date of Patent: Oct. 27, 1998

[54] HIV-1 PROTEASE INHIBITORS

[75] Inventors: Kim D. Janda, San Diego; Peter Wirsching, Solona Beach, both of Calif.

[73] Assignee: The Scripps Research Institute, La Jolla, Calif.

[21] Appl. No.: 667,001

[22] Filed: Jun. 20, 1996

Related U.S. Application Data

[63] Continuation-in-part of Ser. No. 335,039, Feb. 16, 1995, abandoned.

[51] Int. Cl.⁶ ..................................................... C07K 19/00
[52] U.S. Cl. ................................. 514/17; 560/25; 560/26; 546/265; 548/328
[58] Field of Search ............................... 514/17; 560/25, 560/26; 546/265, 280, 328, 334, 335, 245; 548/328, 204, 532

[56] References Cited

U.S. PATENT DOCUMENTS 5,142,056   8/1992   Kempe et al. .......................... 546/265

OTHER PUBLICATIONS

Rich et al., "Effect of Hydroxl in Hydroxethylamine Dipepetide Isosteres On HIV Proteasew Inhibition"S. Med. Chem., (1991) v.34 pp. 1222–1225.

*Primary Examiner*—Cecilia J. Tsang
*Assistant Examiner*—Patrick R. Delaney
*Attorney, Agent, or Firm*—Donald G. Lewis

[57] ABSTRACT

A series of novel oxirane derivatives, which are useful for inhibiting HIV are disclosed. Particularly of value are peptidomimetic compounds, containing a terminal epoxide group on a peptide or psuedopeptide backbone, which are believed to inhibit HIV protease by extruding enzyme-bound water molecules from the active site of the enzyme.

10 Claims, 4 Drawing Sheets

INACTIVATION OF HIV-1 PROTEASE BY

HIV-1 PROTEASE INHIBITORS

This application is a CIP of U.S. Ser. No. 08/335,039, filed Feb. 16, 1995 now abandoned.

BACKGROUND OF THE INVENTION

1. Field of the Invention

This invention relates to novel oxirane compounds which are potent inhibitors of HIV-1 protease.

2. Description of the Related Art

Soon after the discovery that the human immunodeficiency virus (HIV) was the causative agent of acquired immunodeficiency syndrome (AIDS), a number of biochemical pathways required for the replication of such retroviruses were proposed as potential therapeutic targets. HIV is a retrovirus of the Lentiviridae family and two genetically distinct subtypes, HIV-1 and HIV-2, have been characterized.

Among those therapeutic targets, inhibition of the viral reverse transcriptase has been considered a major target in the quest for an effective antiviral agent. Thus, nucleoside-based anti-retroviral agents have been extensively tested clinically against HIV infection. However, the most widely used agents AZT (3'-azido-3'-deoxythymidine), DDC (2',3'-dideoxycytidine), and DDI (2',3'-dideoxyinosine) are all fraught with significant toxicity, and mutations in the viral target can also lead to drug resistance. While non-nucleoside inhibitors of the reverse transcriptase may overcome some of these problems, inhibitors of other essential viral proteins should also be useful as single therapeutic agents or in combination therapy.

The virally encoded protease (HIV-1 PR) is also identified as a site of chemotherapeutic intervention during the viral life cycle. HIV-1 PR is a homodimetric endopeptidase of the aspartyl proteinase family in which each of the identical 99 amino acid subunits contributes a single aspartyl residue to the catalytic site. Except for these two catalytic aspartic acids, the active site of this enzyme can be generally described as an open-ended cylinder which is lined almost exclusively by hydrophobic amino acids. The critical role of proteolytic processing in retroviral replication has been reviewed (e.g., C. U. Hellen et. al., *Biochemistry* 1989, 28, 9981–9890). HIV-1 PR is uniquely responsible for the post-translational cleavage of the viral gag and gag-pol polyproteins into the integrase, reverse transcriptase, protease itself, along with the gag gene 55 kDa polyprotein. The p55 polyprotein is further processed by HIV-1 PR into the structural proteins p17, p24, p7, and p6. Evidence continues to accumulate that viral infectivity is dependent on normal processing at several of the defined cleavage sites. In the absence of a competent protease, the viral reverse transcriptase has either low activity or is enzymatically inert.

At the known cleavage sites of HIV-1 PR, a variety of amino acid sequences have been determined: Tyr-Pro, Leu-Ala, Met-Met, Phe-Leu, Asn-Phe, Phe-Pro, and Leu-Phe dipeptides constitute the scissile bond ($P_1$–$P_1'$ according to the notation of Schecter and Berger: Schechter, I.; Berger, A., *Biochem. Biophys. Res. Commun.*, 1967 27, 157–162). For a review, see Skalka, A. M., *Cell*, 1989 56, 911–913. Substrate-specificity studies also revealed that a minimal size of seven residues, which spans $P_4$–$P_3'$, is required for specific cleavage of the $P_1$–$P_1'$ amide bond. Darkea, P.L., et al., *Biochem, Biophys. Res. Commun.*, 1988 156, 297–303. Despite the lack of an obvious consensus sequence, the nature and identity of residues flanking the $P_1$–$P_1'$ site appear to have considerable influence on a substrate's susceptibility toward hydrolysis.

Current strategies for the design of the HIV-1 PR inhibitors are patterned after the design of inhibitors of renin, an aspartic protease that regulates blood pressure. Existing data indicate in the aspartic protease two aspartic acid groups act with water molecules (enzyme-bound) to cause hydrolysis of the peptide bond (scissile) that is hydrolyzed. D. H. Rich, *J. Med. Chem.*, 1985 28, 263. A tetrahedral diol (I) is believed to be involved as an intermediate for amide hydrolysis.

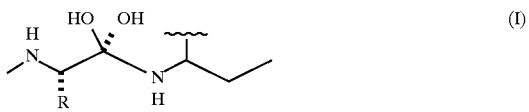

A considerable degree of success has been realized with competitive inhibitors (reversible inhibitors) designed to mimic the transition states leading to (I). The basic concept for this approach is to replace the scissile amide bond with a nonhydrolyzable bond in an appropriate sequence context. Peptidomimetic inhibitors have been reported that substitute the hydroxyethylene, hydroxyethylamine, or phosphoric acid dipeptide isosteres of P1–P'1 for the scissile peptide bond found in substrates. For example, the hydroxyethylene isostere was used successfully by J. P. Vacca, et al. (*J. Med. Chem.* 1991, 34, 1225) to generate highly potent inhibitors of HIV-1 PR. Another group of inhibitors incorporating a hydroxyethylamine isostere moiety possess high potency against both HIV-1 and HIV-2 proteases (N. A. Roberts et al., *J.C. Science*, 1990, 248, 358). Use of a phosphinate as a transition state mimic also led to highly potent inhibitors of HIV-1 and HIV-2 protease. Grobelny, D., et al., *Biochem. Biophys. Res. Commun.* 1990, 169, 1111. On the contrary, introduction of reduced amide isostere provide compounds with weak activity. A different approach to HIV-1 PR inhibitors has recently been reported in which the unique $C_2$ symmetry of the active site of the enzyme is utilized. D. J. Kempf et al. prepared a number of very potent symmetric and pseudosymmetric inhibitors (*J. Med. Chem.* 1990, 33, 2687).

In contrast to the progresses in the design of reversible inhibitors, attempts to find irreversible inhibitors have yielded only week inhibitors. The known antifungal antibiotic cerulenin was found to weakly inhibit both HIV-1 PR and HIV-2 PR (J. J. Blumenstein et al., *J. Biochem. Biophys. Res. Commun.* 1989, 163, 980). Cerulenin has the following formula:

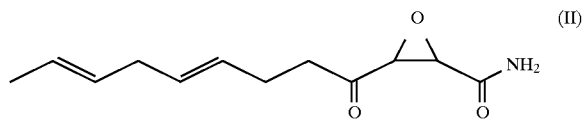

Data from preincubation experiments support the proposal that the epoxy amide slowly inactivated the enzyme, presumably, by esterification of a catalytic aspartate residue through epoxide opening ("irreversible"). Moelling, K., et al., *FEBS Lett.*, 1990, 261, 373.

Although some degree of success has been achieved in the above-identified protease inhibitors, there is a definite need to provide potent and specific HIV PR inhibitors which can be used alone or in combination with therapy with drugs directed toward different targets in the viral life cycle. This invention addresses the much-sought need of availability of such HIV-1 PR inhibitors.

SUMMARY OF THE INVENTION

It has now been discovered that certain novel compounds which are characterized by having a terminal epoxide moiety possess exceptional value as HIV-1 PR inhibitors.

Generally, these compounds may be represented by the following three groups of terminal epoxides.

A first group of compounds of the present invention are of the formula:

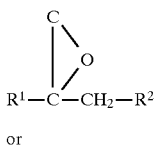
(III A)

or

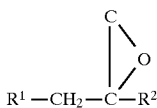
(III B)

or a pharmaceutically acceptable salt thereof,
wherein R1 is hydrogen, $C_1$–$C_7$ alkyl or $X^1$–$Y^1$ and $R^2$ is hydrogen, $C_1$–$C_7$ alkyl or $Y^2$–$X^2$,
wherein $X^1$ is an N-terminating group, $X^2$ is an C-terminating group and $Y^1$ and $Y^2$ are each an amino acid residue or an oligopeptide containing a sequence of up to five amino acid residues, with the provision that neither $R^1$ in formula (III) nor $R^2$ in formula (IV) is hydrogen.

Also, individually preferred compounds within the the first group are represented by the following formulae:

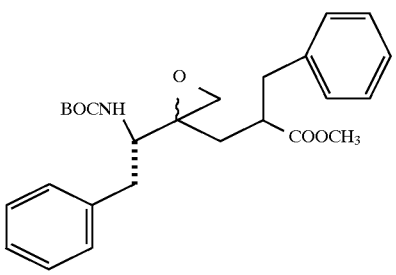
(IV A)

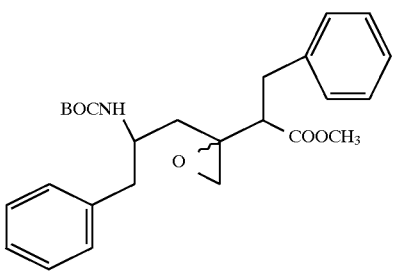
(IV B)

A second group of compounds of the present invention are of the formula:

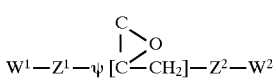
(V A)

or

(V B)

or a pharmaceutically acceptable salt thereof,
wherein $Z^1$ is a $P_1$–$P_n$ peptide sequence of a peptide substrate proteolytically hydrolyzable by a human immunodeficiency virus protease; $Z^2$ is a $P_1'$–$P_m'$ peptide sequence of a peptide substrate proteolytically hydrolyzable by a human immunodeficiency virus protease; the notation of ψ[ ] indicates the 1-epoxyethylene group in the bracket replaces a peptidyl amide bond between the $P_1$–$P_1'$ residues; $W^1$ is an N-terminating group; and $W^2$ is an C-terminating group,
wherein m and n are each an integer of from 1 to 5 and the $P_1$–$P_n$ and $P_1'$–$P_m'$ are the peptide sequence notation of Schecter and Berger.

A third group of compounds of the present invention are of the formula:

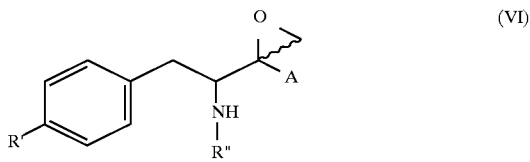
(VI)

or a pharmaceutically-acceptable salt thereof,
wherein R' is hydrogen, hydroxyl or a protected hydroxyl;
R" is an amino protecting group or U-V,
wherein U is an oligopeptide containing a sequence of up to four amino acid residues and V is an N-terminating group;
and A is selected from the group consisting of:
(a) $C_1$–$C_8$ alkyl;

(b)

wherein $R^3$ is $C_1$–$C_5$ alkyl, $C_7$–$C_9$ phenylalkyl, $C_{11}$–$C_{13}$ naphthylalkyl, $C_8$–$C_{10}$ phenylalkenyl; and $R^4$ is a carboxyl protecting group, a protected amino group or S-T,
wherein S is an oligopeptide containing a sequence of up to four amino acid residues and T is a C-terminating group;

(c)

wherein o is 1 or 2; and $R^5$ is a carboxyl protecting group a protected amino group or O-Q,
wherein O is an oligopeptide containing a sequence of up to four amino acid residues and Q is a C-terminating group; and

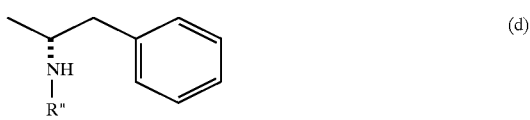
(d)

wherein R' and R" are as previously defined.

The present invention also encompasses pharmaceutical compositions containing a human immunodeficiency virus protease-inhibiting amount of a compound represented by one of the formulae: (III A), (III B), (V A), (V B), and (VI) together with a pharmaceutically acceptable carrier.

Also embraced by the present invention is a method for inhibiting the cleavage of the gag and gag-pol polyproteins of a human immunodeficiency virus by a human immunodeficiency virus protease 1 in the body of a host, which comprises administering to the host, an effective amount of a terminal epoxide compound that binds to the carboxyl groups of Asp-25 and Asp-225 of the protease by extruding enzyme-bound water molecules from the active site formed by the aspartic acid residues.

Preferred compounds used in the practice of the above-indicated method are a compound represented by one of the formulae (III A), (III B), (V A), (V B), and (VI).

Additionally, the present invention includes intermediate compounds of the formula:

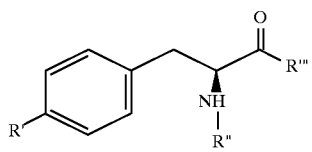

(VII)

wherein R' and R" are as previously defined, and R''' is $C_1$–$C_8$ alkyl.

Finally, the present invention includes a process for preparing a compound of formula (VI) wherein A is $C_1$–$C_8$ alkyl, which comprises contacting a compound of formula (VII) with a methylene sulfur ylide, in the presence of a reaction-inert solvent at a temperature of about −10° to about 50° C.

DETAILED DESCRIPTION OF THE INVENTION

Figure 1:
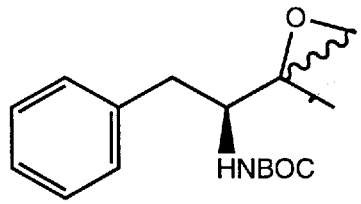
FIG. 1 illustrates the inactivation of HIV-1 protease in the presence of a protease inhibitor of this invention.
Figure 1:
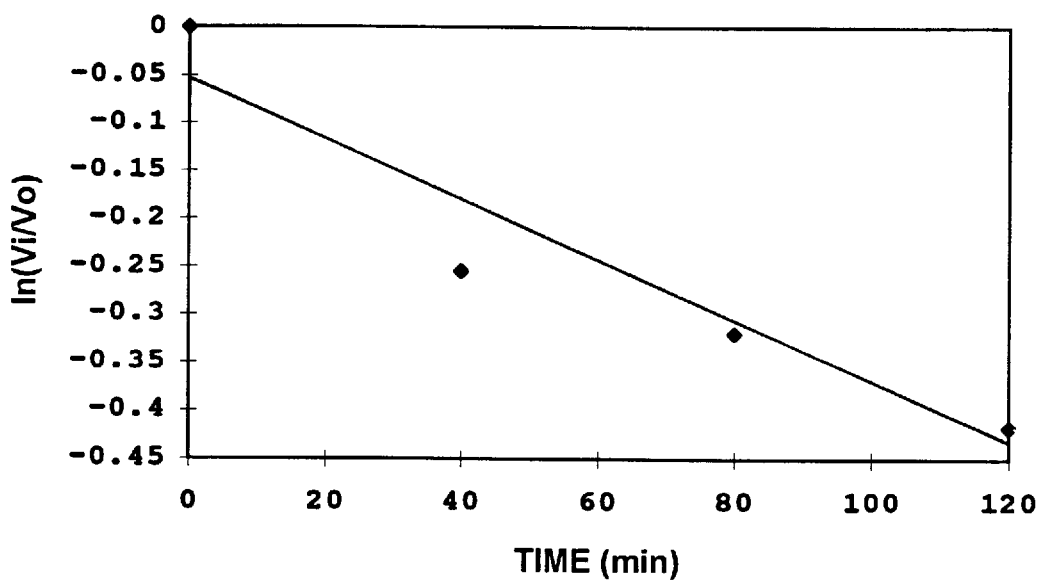

The present invention relates to terminal epoxide compounds that reversibly bind to and competitively inhibit the activity of HIV-1 PR.

As used herein, the term "terminal epoxide" refers to an epoxide compound wherein the epoxide group is attached to a quaternary carbon atom in the molecule.

The expression "pharmaceutically acceptable salts" used herein refers to acid addition salts of any of the compounds of the formulae (III A) -(VI) which contain a basic functionality with an acid such as (but not limited to) hydrochloric acid, nitric acid, sulfuric acid, phosphoric acid, methanesulfonic acid, p-toluenesulfonic acid, acetic acid, or succinic acid. When the present compounds contain more than one basic function, the salts optionally contain more than one equivalent of acid. Alternatively, when the present compounds contain an acidic functionality, the expression also refers to cationic salts such as (but not limited to) an alkali metal salt (e.g., sodium, potassium), an alkaline earth salt (e.g., magnesium, calcium), or an amine salt (e.g., diethanolamine, meglumine). Conventional methods are used to prepare such salts.

The expression "N-terminating group" used herein refers to those groups that are conventionally used to terminate an amino group in the peptide chemistry. Examples of suitable N-terminating groups include hydrogen, $R^6$, and $R^6CO$ wherein $R^6$ is selected from linear, branched, unsubstituted and substituted $C_1$–$C_8$ lower alkyls, $C_2$–$C_8$ alkenyls, $C_2$–$C_8$ alkynyls, $C_6$–$C_{14}$ cycloalkyls, and $C_6$–$C_{10}$ aryls. The particularly preferred groups are Ac, Boc (tert-butyloxycarbonyl), Cbz (benzyloxycarbonyl), Noa (1-napthyloxyacetyl), and Qc (quinolin-2-ylcarbonyl).

The expression "C-terminating group" used herein refers to those groups that are conventionally used to terminate a carboxyl group in the peptide chemistry. Examples of suitable C-terminating groups include $OR^7$ (including hydroxyl), —$NR^7_2$ (including —$NH_2$ and $NHR^7$), —$NHNH_2$ and —$SR^7$ wherein $R^7$ is selected from $C_1$–$C_8$ lower alkyls, $C_2$–$C_8$ alkynyls, $C_6$–$C_{14}$ cycloalkyls, $C_6$–$C_{10}$ aryls and in the case of $NR^7_2$, from cyclized groups forming (in attachment with the nitrogen atom) a 5–8 membered heterocyclic ring optionally containing oxygen, nitrogen or sulfur as a further ring heteroatom. The particularly preferred C-terminating groups are amino, benzylamino, $C_1$–$C_3$ alkoxy, and Amp (2-pyridylmethylamine).

The expression "amino protecting group" used herein refers to those groups that are conventionally used to protect an amino moiety in the organic chemistry. The expression is interchangeably used with the expression "N-terminating group".

The expression "carboxyl protecting group" used herein refers to those groups that are conventionally used to protect a carboxyl moiety in the organic chemistry. The expression is interchangeably used with the expression "C-terminating group".

The expression "protected hydroxyl" used herein refers to a hydroxyl group protected by any conventional hydroxyl protecting group that does not possess detrimental effect of the protease-inhibiting activity of the present compounds. Exemplary such hydroxyl protecting groups include alkanoyl having 2 to 5 carbons, such as acetyl; aryloyl having 7 to 11 carbons, such as benzoyl; benzyl; 1-ethoxyethyl; methoxymethyl; and 4-methoxyphenylmethyl.

The expression "protected amino group" used herein refers to amino groups that are protected by the amino protecting groups enumerated above. In the case of $R^4$ in formula (VII) being a protected amino group, the group embraces amino derivatized with groups that would enhance HIV-protease inhibiting activity. The particularly preferred groups for the purpose of enhancement of HIV protease inhibiting activity are benzylamino, 1(S)-indanylamino, 1(R)-indanylamino, 2(R)-hydroxyl-1(S)-indanyl amino and 2(S)-hydroxyl-3-(R)-hydroxyl-1(S)-indanylamino.

The expression "oligopeptide" used herein refers to a peptide (including a single amino acid) containing a sequence of up to about five amino acid residues and further to a peptidomimetic compound containing (including a single amino acid mimetic compound) a sequence of up to about five amino acid (amino acid mimetic compound) residues The terminal epoxides of the present invention is postulated to bind to a HIV-1 PR by extrusion of enzyme-bound water from the active site formed by Asp-25 and Asp-225 in HIV-1 PR. A possible collected-substrate mechanism can be proposed for inhibition of HIV-1 PR by the terminal epoxides as follows:

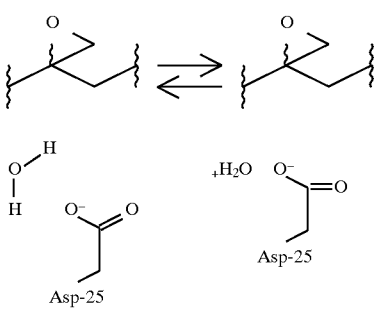

This mechanism is in analogy to that proposed for inhibition of aspartic proteases by statine-derived inhibitors. Rich D. H., et al., *Biochemistry*, 1985, 24, 3165–3173. When the terminal epoxide of the present invention comes in contact with the space between the two aspartic acid carboxyl groups, a bound water molecule is displaced from the active site to bulk solvent, as shown in the above scheme. This extrusion of water increases the interaction between the enzyme and the epoxide by increasing the entropy of water. Being such a collected-substrate inhibitor, the epoxides of the present invention reversibly bind to HIV-1 PR to form an enzyme-inhibitor complex.

The terminal epoxides of the present invention include peptidomimetic compounds of formula (V A) or formula (V B). In the formulae, the "psi bracket" ($\psi[\ ]$) is used to designate a peptidyl amide bond being replaced by a 1-epoxy-ethylene group in the bracket. Specifically, "hyphens" between amino acid residues indicate the presence of a peptidyl amide bond. "Hyphens" adjacent to the $\psi$ symbol or to the brackets mean the presence of a carbon-carbon bond. See Spatola, *Chemistry and Biochemistry of Amino Acids, Peptides, and Proteins*; Weinstein, ed.; Marcel Dekkar, Inc.; New York, 1983, vol., 7, chapter 5; pp 267–357. The term "peptidomimetic" as used herein, refers to a peptide analog having a peptide backbone modification.

A compound of formula (V A) or formula (V B) contains a 1-epoxy-ethylene group as a surrogate bond for a peptidyl amide bond which is hydrolyzable by HIV-PR. The term "surrogate" refers to an unnatural replacement such as the 1-epoxy-ethylene group for a scissile peptidyl amide bond.

According to the formulae (V A) and (V B), the crucial surrogate bond is flanked by radicals $Z^1$ and $Z^2$. $Z^1$ and $Z^2$ represent a $P_1-P_n$ sequence and a $P'_1-P'_m$ sequence of a peptide substrate (natural or unnatural) proteolytically hydrolyzable by HIV-1 PR. In the Schechter and Berger notation, a peptide substrate is numbered in two directions from the scissile bond. The amino acid residues of the dipeptide portion that is cleaved are numbered $P_1$ and $P_1'$ such that after cleavage, the $P_1$ residue becomes the carboxy-terminal residue of one cleaved portion and the $P_1'$ residue becomes the amino-terminal residue of the other portion.

The remaining residues of the $P_1'$-containing portion are numbered $P_2'$, $P_3'$, $P_4'$. . . and so on toward the carboxy-terminus ($P_m'$). The remaining residues of the $P_1$-containing portion are numbered toward the amino-terminus of that portion ($P_m$) as $P_2$, $P_3$, $P_4$. . . and so on. The dipeptide portion of a substrate oligopeptide that is cleaved is thus defined as $P_1-P_1'$. The Schechter and Berger notation is utilized whether or not the bond linking the $P_1$ and $P_1'$ residues is a peptide bond or is capable of hydrolytic cleavage. In the formula m and n are each an integer of from 1 to about 5. Preferably, both m and n are from about 3 to 5.

Following the above nomenclature, residues $P_1$ and $P_1'$ of a contemplated peptidomimetic compound described herein are joined by the 1-epoxy-ethylene group. The $P^1$ position residue is thus considered to be an amino acid residue even though the carboxyl group normally present is replaced by a quartery carbon bearing an epoxide moiety. By the same token, the $P_1'$ position is also considered to be an amino acid residue even though the amino group normally present is replaced by a methylene moiety. Alternatively, the $P_1$ carboxyl group can be replaced by methylene moiety, and the $P_1'$ amino group can be replaced by the epoxide group. For the $P_1$ and $P_1'$ positions, standard amino acid residue notations are used throughout the specification.

The groups $W^1$ and $W^2$ represent an N-terminating group and an C-terminating group, respectively. Each of $W^1$ and $W^2$ can be selected from the afore-indicated terminating groups.

The overall length of a contemplated peptidomimetic compound is 2 to about 10 amino acid residues.

Although any amino acid residue can be present in $Z^1$ and $Z^2$, hydrophobic amino acid residues are preferred, particularly for the $P_1$ and $P_1'$ positions. Met, Phe, and Tyr are preferred at $P_1$. Branched amino acids such as Val and Ile are preferred at the $P_2$ and $P_2'$ positions.

Where amino acid residues are used herein without an indication of enantiomeric structure, either a L- or D-enantiomer may suitably be utilized, although the L-enantiomer is preferred for amino acids having the normal peptide bond orientation, and the D-enantiomer is preferred for amino acids having a reversed orientation. Additionally, analogs of amino acids and amino acid mimetic compounds may be employed in place of natural amino acid residues. Exemplary compounds include β-alanine, α-aminoisobutyric acid, homoarginine, homoproline, homoserine, norarginine, norleucine, ornithine, and p-nitrophenylalanine.

The N- or C-terminating groups are preferably present in a contemplated peptidomimetic compound. First, their presence removes ionic charge from the peptidomimetic compound to help facilitate passage through membranes. Second, they protect the compound from degradation by other proteases in the in vivo environment. Third, they may be used to alter bioactivity, solubility and/or biodistribution characteristics of the subject compound.

The peptidomimetic compounds of the present invention are generally modeled after amino acid sequence occurring in HIV-1 gag and gag-pol polyprotein precursor molecules (substrates).

Although the inventors do not intend to limit the present invention to any particular mechanism of activity, it is presently believed that the peptidomimetic compounds are involved in vivo in binding to Asp-25, Asp-225 of HIV-1 PR as well as to the backbone of the protease through multiple hydrogen bondings and van der Waals contact. Therefore, it is normally preferred that the peptidomimetic compounds contain the amino acid residues that appear in the corresponding positions of the known substrate molecules.

The preferred values of $Z^1$ are a partial or whole sequence having $P_1-P_5$ of:

| $P_5$ | $P_4$ | $P_3$ | $P_2$ | $P_1$ |
|---|---|---|---|---|
| Val | Ser | Gln | Asn | Tyr |
| Lys | Ala | Arg | Val | Leu |
| Thr | Ala | Thr | Ile | Met |
| Arg | Pro | Gly | Asn | Phe |
| Glu | Arg | Gln | Ala | Asn |
| Val | Ser | Phe | Asn | Phe |

-continued

| $P_5$ | $P_4$ | $P_3$ | $P_2$ | $P_1$ |
|---|---|---|---|---|
| Cys | Thr | Leu | Asn | Phe |
| Ile | Arg | Lys | Ile | Leu |

Similarly, the preferred values of $Z^2$ are a partial or whole sequence having $P_1'-P_5'$ of:

| $P_1'$ | $P_2'$ | $P_3'$ | $P_4'$ | $P_5'$ |
|---|---|---|---|---|
| Pro | Ile | Val | Gln | Asn |
| Ala | Glu | Ala | Met | Ser |
| Met | Gln | Arg | Gly | Asn |
| Leu | Gln | Ser | Arg | Pro |
| Phe | Leu | Gly | Lys | Ile |
| Pro | Gln | Ile | Thr | Leu |
| Pro | Ile | Ser | Pro | Ile |
| Phe | Leu | Asp | Gly | Ile |

Individually preferred compounds are as follows:
$CH_3C(O)$-Ser-Leu-Asn-Pheψ[ ] Pro-Ile-Val-$OCH_3$ (SEQ ID NO 1)
$C_5H_{11}C(O)$-Ser-Leu-Asn-Pheψ[ ] Pro-Ile-Val-$OCH_3$ (SEQ ID NO 2)
$CH_3C(O)$-Ser-D-Leu-Asn-Pheψ[ ] Pro-Ile-Val-$OCH_3$
$CH_3C(O)$-Ser-Leu-Asn-Tyrψ[ ] Pro-Ile-Val-$OCH_3$ (SEQ ID NO 3)
$CH_3C(O)$-Ser-Leu-Asn-Pheψ[ ] PIC-NH-$^t$Bu* (SEQ ID NO 4)
$CH_3C(O)$-Ser-Leu-Asn-Pheψ[ ] DIQ-NH-$^t$Bu* (SEQ ID NO 5)
$CH_3C(O)$-Leu-Asn-Pheψ[ ] PIC-NH-$^t$Bu*
$CH_3C(O)$-Leu-Asn-Pheψ[ ] DIQ-NH-$^t$Bu*
QC-Asn-Pheψ[ ] PIC-NH-$^t$Bu*
QC-Asn-Pheψ[ ] DIQ-NH-$^t$Bu*

*QC=quinoline-2-carbonyl; PIC=piperidine-2(S)-carbonyl; DIQ=(4aS,8aS)-decahydro-3(S)-isoquinoline carbonyl; PIC and DIQ are analogs of proline; $^t$Bu=tert-butyl; and ψ[ ] represents ψ[1-epoxy-ethylene].

However, as it will be appreciated, substitutions of amino acids in particular positions may be employed to preserve or even increase the HIV protease inhibiting activity of the subject peptidomimetic compounds. Specifically, where any known HIV-PR substrates (partially or wholly) are to be employed in the present invention, one or more such substitutions in the native sequence will not drastically alter the contemplated inhibiting activity. Those practicing the present invention will be able to evaluate substitution choices as described herein by applying the principles of functional group conservation, as recognized by the art, and by employing the assay techniques provided herein.

In another aspect of the present invention, the terminal epoxide-containing compounds may be represented by formula (III A) or formula (III B).

A preferred $Y^1$ within the scope of the formulae (III A) and (III B) is a peptide selected from the sequence:

| 1- | 2- | 3- | 4- | 5- |
|---|---|---|---|---|
|  | 2- | 3- | 4- | 5- |
|  |  | 3- | 4- | 5- |
|  |  |  | 4- | 5- |
|  |  |  |  | 5- | wherein 1 is selected from His, Lys, Ser, Thr, and Ser;
2 is selected from Ala, His, Glu, Gly, Pro, and Ser;
3 is selected from Ala, Arg, Asp, Gln, Leu, Phe, Ser, Thr, and Val;
4 is selected from Ala, Asn, Gln, His, Ile, Phe, and Val;
5 is selected from Ala, Asn, Leu, Nle, Phe, Tyr, and Val.

Highly preferred peptide sequences are:
5 (Phe);
4 (Asn) 5 (Phe);
4 (Val) 5 (Val);
3 (Leu) 4 (Asn) 5 (Phe);
3 (Phe) 4 (Phe) 5 (Phe);
3 (Ala) 4 (Ala) 5 (Phe);
3 (Val) 4 (Val) 5 (Phe);
3 (Phe) 4 (His) 5 (Leu);
3 (Ser) 4 (Ala) 5 (Ala);
3 (Ser) 4 (Ala) 5 (Ala);
3 (Ser) 4 (Gln) 5 (Asn);
3 (Thr) 4 (Ile) 5 (Nle);
2 (Ser) 3 (Gln) 4 (Asn) 5 (Phe) (SEQ ID NO 6);
2 (Ser) 3 (Ala) 4 (Ala) 5 (Phe) (SEQ ID NO 7);
2 (Val) 3 (Ser) 4 (Glu) 5 (Asn) (SEQ ID NO 8);
2 (Ser) 3 (Leu) 4 (Asn) 5 (Phe) (SEQ ID NO 9);
1 (Val) 2 (Ser) 3 (Gln) 4 (Asn) 5 (Leu) (SEQ ID NO 10);
1 (Val) 2 (Ser) 3 (Gln) 4 (Asn) 5 (Phe) (SEQ ID NO 11); and
1 (His) 2 (Pro) 3 (Phe) 4 (His) 5 (Val) (SEQ ID NO 12).

A preferred $Y^2$ within the scope of formulae (III A) and (III B) is a peptide selected from the sequence:

| — | 6 |  |  |  |
|---|---|---|---|---|
| — | 6- | 7 |  |  |
| — | 6- | 7- |  |  |
| — | 6- | 7- | 8 |  |
| — | 6- | 7- | 8- | 9 |
| — | 6- | 7- | 8- | 9- | 10 | wherein 6 is selected from Ala, Gly, Leu, Nle, Nph, Phe, Pro, and Val;
7 is selected from Gln, Glu, Ile, Leu, Thu, and Val;
8 is selected from Ala, Amp, Arg, Gly, Glu, Phe, and Val;
9 is selected from Ala, Asn, Gln, Lyn, and Nle; and
10 is selected from Ala, Gly, and Phe.

Highly preferred peptide sequences are:
6 (Phe);
6 (Pro);
6 (Val) 7 (Ile);
6 (Ile) 7 (Val);
6 (Val) 7 (Val);
6 (Pro) 7 (Ile) 8 (Val);
6 (Pro) 7 (Val) 8 (Val);
6 (Phe) 7 (Val) 8 (Val);
6 (Phe) 7 (Leu) 8 (Phe);
6 (Val) 7 (Ile) 8 (Val);
6 (Val) 7 (Ile) 8 (His);
6 (Gly) 7 (Val) 8 (Val); and
6 (N Ile) 7 (Gln) 8 (Arg).

As with the peptidomimetic compounds of formula (V A) and formula (V B), the N- and/or C-terminating groups are preferably employed at one or more terminuses of the compounds of formula (III A) or formula (III B).

A first group of the compounds of formula (VI) are represented by the formula:

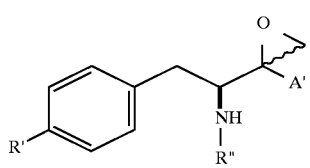

wherein A' is $C_1$–$C_8$ alkyl; and R' and R" are as previously defined.

Preferred within this first group are compounds (VII A) wherein R' is hydrogen, R" is selected from Ac, Bz, Boc, Cbz and Tba, and A is methyl. Also preferred are those compounds where R' is hydrogen and R" is an amino acid sequence selected from Asn, His, Phe, Val, Ile-Thr, Ala-Ala, Phe-Phe, Val-Val, His-Phe, Ala-Ala-Ser, Asn-Leu-Ser, Asn-Gln-Ser-Val (SEQ ID NO 13) and His-Phe-Pro-His (SEQ ID NO 14). When R" is an oligopeptide, the N-terminus of the oligopeptide is preferably protected by a group selected from Ac, Boc, Cbz, Noa and Qc.

A second group of the compounds of formula (VI) are represented by the formula:

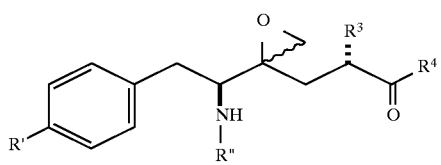

wherein R', R", $R^3$ and $R^4$ are as previously defined.

Preferred within this second group are compounds wherein R' is hydrogen and R" is selected from the group consisting of Ac, Bz, Boc, Cbz and Tba.

Especially preferred are those compounds where $R^3$ is selected from the group consisting of isopropyl, isobutyl, benzyl, cinnamyl and naphthyl. Also preferred are those compounds where $R^4$ is selected from the group consisting of benzylamino, 1(S)-indanylamino, 1(R)-indanylamino, 2(R)-hydroxyl-1(S)-indanylamino and 2(S)-hydroxyl-3(R)-hydroxyl-1(S)-indanylamino.

Further preferred are those compounds where $R^4$ is an amino acid sequence selected from Ile, Leu, Leu-Phe, Ile-His and Val-Val. When $R^4$ is an oligopeptide, the C-terminus of the oligopeptide is preferably protected by a group selected from amino, benzylamino, $C_1$–$C_3$ alkoxy, Amp and Ambi (2-(aminomethyl) benzimidazole).

A third group of the compounds of formula (VI) are represented by the formula:

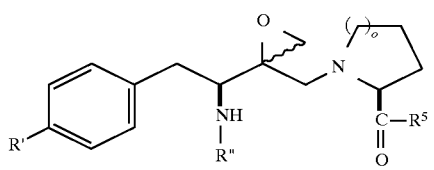

wherein R', R", o and $R^5$ are as previously defined.

Preferred within this third group are compounds wherein R' is hydrogen and R" is selected from the group consisting of Ac, Bz, Boc, Cba and Tba. Especially preferred are those compounds where o is 1 and $R^5$ is t-butoxy or an amino acid sequence selected from Ile-Val and Val-Val. When $R^5$ is an oligopeptide, the C-terminus of the oligopeptide is preferably protected by amino or $C_1$–$C_3$ alkoxy. When R" is an oligopeptide, it is preferably selected from Asn, His, Phe, Val, Ile-Thr, Ala-Ala, Phe-Phe, Val-Val, His-Phe, Ala-Ala-Ser, Asn-Leu-Ser, Asn-Gln-Ser-Val (SEQ ID NO 13), and His-Phe-Pro-His (SEQ ID NO 14). The N-terminus of the oligopeptide is preferably protected by a group selected from Ac, Boc, Cvz, Noa, and Qc.

Also preferred within this third group are compounds where o is 2 and $R^5$ is t-butylamino.

A fourth group of compounds of the formula (VI) are represented by the formula:

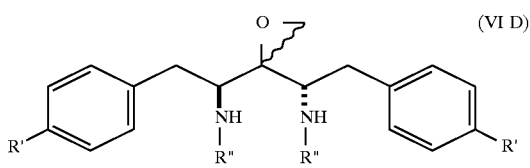

wherein R' and R" are as previously defined.

Preferred within this fourth group are compounds wherein R' is hydrogen and R" is selected from Ac, Bz, Boc, Cbz and Tba. Also preferred are compounds wherein R' is hydrogen and R" is an oligopeptide selected from Asn, His, Phe, Val (SEQ ID NO 13), Ile-Thr, Ala-Ala, Phe-Phe, Val-Val, His-Phe, Ala-Ala-Ser, Asn-Leu-Ser, Asn-Gln-Ser-Val, and His-Phe-Pro-His (SEQ ID NO 14). When R" is an oligopeptide, the N-terminus of the oligopeptide is preferably protected by a group selected from Ac, Boc, Cbz, Noa and Qc.

The synthesis of the compounds of the present invention is relatively straight forward inasmuch as most of the molecular structure is constituted by oligopeptides (or pseudopeptides).

The peptide portions of the compounds of the present invention may be synthesized by the solid phase peptide synthesis (or Merrifield) method, by solution phase synthesis, or by other techniques known in the art. The Merrifield synthesis established and widely used, and experimental procedures, are described in the following references: Merrifield, J. Am. Chem. Soc., 1963, 85, 2149–2154; Meienhofer, J., In Hormonal Proteins and Peptides; Li, C.H., Ed; Academic Press: New York, 1973; Vol. 2; pp. 48–267; Barany and Merrifield In The Peptides; Gross, E., and Meienhofer, J; Academic Press: New York, 1983; Vol. 2; pp. 3–285.

In this preferred method a peptide of any desired length and of any desired sequence is produced through the stepwise addition of amino acids to a growing peptide chain which is bound by a covalent bond to a solid resin particle. Automated synthesis may be employed in this method.

In the preferred application of this method the C-terminus of the growing peptide chain is covalently bound to a resin particle and amino acids having protected amino groups are added in the stepwise manner indicated above. A preferred amino protecting group is the t-Boc group, which is stable to the condensation conditions and yet is readily removable without destruction of the peptide bonds or racemization of chiral centers in the peptide chain. At the end of the procedure the final peptide is cleaved from the resin, and any remaining protecting groups are removed, by treatment under acidic conditions, such as, for example, with a mixture of hydrobromic acid and trifluoroacetic acid, with trifluoromethane sulfonic acid or with liquified hydrofluoric acid.

The cleaved peptides are isolated and purified by means well known in the art such as, for example, lyophilization following, for example, reversed phase (preferably) or normal phase high pressure liquid chromatography (HPLC), or by either size exclusion or partition chromatography on polysaccharide gel media such as Sephadex G-25, or countercurrent distribution. The composition of the final peptide may be confirmed by amino acid analysis after degradation of the peptide by standard means, by amino acid sequencing techniques, or by FAB-MS techniques.

Salts of carboxyl groups of the peptide may be prepared in the usual manner by contacting the peptide with one or more equivalents of a desired base such as, for example, a metallic hydroxide base, e.g., sodium hydroxide; a metal carbonate or bicarbonate base such as, for example, sodium carbonate or sodium bicarbonate; or an amine base such as, for example, triethylamine, triethanolamine, and the like. In all such procedures and in other synthetic procedures provided herein, the pH should be kept below approximately 8 in order to avoid complications such as racemization, demamidation, peptide degradation or other undesirable side reactions.

Acid salts of the peptides may be prepared by contacting the peptide with one or more equivalents of the desired inorganic or organic acid, such as, for example, hydrochloric acid, acetic acid or citric acid.

Esters of carboxyl groups of the peptides may be prepared by any of the usual means known in the art for converting a carboxylic acid or precursor to an ester. One preferred method for preparing esters of the present polypeptide, when using the Merrifield synthesis technique described above, is to cleave the completed polypeptide from the resin in the presence of the desired alcohol either under basic or acidic conditions, depending upon the resin. Thus the C-terminus of the peptide when freed from the resin is directly esterified without isolation of the free acid. Alternatively, especially where the desired peptide contains one or more glutamic acid or aspartic acid residues, C-terminal amino acid esters may be made using solution phase synthesis wherein the C-terminal residue bearing the desired ester functionality is incorporated.

Amides of the peptides of the present invention may also be prepared by techniques well known in the art for converting a carboxylic acid group or precursor to an amide. A preferred method for amide formation at the C-terminal carboxyl group is to synthesize the peptides by solid phase methods on a benzhydrylamine resin, and thereafter to cleave the polypeptide from a solid support with an appropriate acid. If the desired amide is to include a secondary or tertiary amino group, then the amide may be synthesized using solution phase techniques wherein an amidated C-terminal residue bearing the desired amide functionality is incorporated.

N-Acyl derivatives of an amino group of the present polypeptides may be prepared by utilizing an N-acyl protected amino acid for the final condensation, or by acylating a protected or unprotected peptide. Acylation may be carried out using standard acylating reagents such as acyl halides, anhydrides, acyl imidazoles, and the like prior to deprotection of the residue side chains.

The coupling, deprotection/cleavage reactions and preparation of derivatives of the subject polypeptides are suitably carried out at temperatures between about −10 20 and +80° C., most preferably about 20°–25° C. The exact temperature for any particular reaction will, of course, be dependent upon the substrates, reagents, solvents and so forth, all being well within the skill of the practitioner.

The peptides of the present invention may also be synthesized using any techniques that are known to those in the peptide art, for example, those described in Houben Weyl, Methoden Der Organischen Chemie; Georg-Thieme-Verlag, Stuttgart 1974, Vol. 15-II, pp. 1–806.

The required terminal epoxide portion may be introduced to the backbone of the compounds of the present invention by methods familiar to those skilled in the art. Generally, a precursor of the compound of the present invention is subjected to epoxidation.

This epoxide introduction can be accomplished in a number of ways. However, for purposes of illustrative clarity and ease of comprehension, only a few of the preferred group of compounds will be referred to hereinafter. It should be understood, however, that the use of this particular series of compounds for descriptive purpose shall not restrict nor limit the scope of the appended claims. For example, an exo-olefin of formula (VIII) can be converted to the epoxide compound of formula (VI) by an epoxidation method known in the art. Thus, epoxidizing agents that can be used include hydrogen peroxide in the presence of a metal catalyst, peracetic acid, perbenzoic acid, m-chloroperbenzoic acid, monoperphthalic acid and others. For methods and reaction conditions, see, for example, Swern D., *Org. Reactions*, 1953, 7,378.

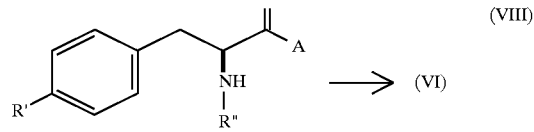

wherein R' and R" are as previously defined.

Alternatively, a ketone of formula (VII) can be converted to the compound of formula (VI) by reacting with a methylene sulfur ylide, e.g.,

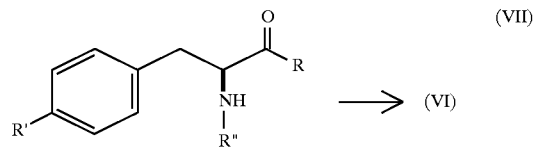

For general methods and reaction conditions, see, for example, *Tetrahedron*, 1980, 36, 2531. This reaction may be carried out in a reaction-inert solvent, employing dimethylsulfonium methylide. Preferred solvents are polar, aprotic solvents such as dimethylformamide, diethylformamide, N-methyl-2-pyrrolidone or dimethylsulfoxide. The particularly preferred solvent is dimethylsulfoxide. Further it is preferred that the reaction be carried out in the presence of a base. Such bases include alkali and alkaline earth metal hydrides. The preferred base is sodium hydride. The required dimethylsulfonium methylide is generated in situ from an appropriate precursor molecule, such as trimethylsulfonium iodide.

In practice, the dimethylsulfonium methylide is added to the ketone (VII) and base in the appropriate solvent. It is preferable to employ for one mole of the ketone about a molar equivalent of the dimethylsulfonium methylide and the base, with the best results achieved by using just a slight excess of each. It is preferred that the reagents be combined in the cold, generally from −10° to 0°, and the reaction mixture be maintained at that temperature. Heating is possible at from room temperature to about 50° C., but is not generally necessary. Reaction proceeds to completion in about a half hour to overnight depending on the reactivity of the ketone.

Upon completion of the reaction, the product is isolated by addition of the mixture to brine. The product can be filtered or extracted with a water immiscible solvent. Purification can be done by chromatography or by recrystallization from an appropriate solvent.

For the purpose of the conversion of the ketone (VII) to the compound of formula (VI), other methylene sulfur ylides such as dimethylsulfoxonium methylide can be used with similar results (Corey, E. J., et al., *J. Am. Chem.*, 1964, 84, 867). Further, a nucleophilic methyl transfer reagent may replace the methylene sulfur ylide. Exemplary methyl transfer reagents are methylphenyl-N-p-toluenesulfoximine anion (Johnson, C. R., et al., *J. Am. Chem. Soc.*, 1970, 92, 5753), and phenylthiomethyl anion (Shanklin, J. R., et al., *J. Am. Chem. Soc.*, 1973, 95, 3429). Since the epoxide formation employed above is not enantioselective, the product epoxides of formula (VI) are diasteriomeric. Thus, the present invention embraces diasteriomeric mixture and optically pure forms of the epoxide as represented by formula (VI).

The required ketone (VII) may be synthesized in the following manner:

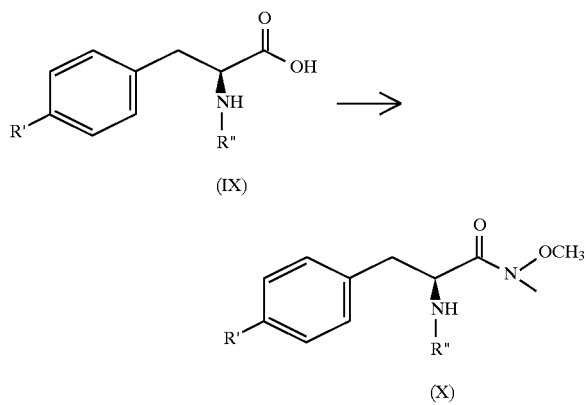

The starting compound (IX) is obtained commercially or by standard methods well known in the art. When the compound of formula (IX) contains an oligopeptide as R", an appropriate N-protected amino acid or its derivative is used as a reactant in the first coupling step to build the oligopeptide portion. Prior to coupling reactions, a carboxylic function in the compound of formula (IX) is preferably protected by a suitable protecting group such as benzyl, and $C_1$–$C_4$ alkyl. Preferred coupling conditions employ more or less equimolar quantities of the reagents to be coupled, dicyclohexylcarbodiimide (or a similar dehydrative coupling agent) in an equimolar quantity and 1-hydroxybenzotriazole in 1–2 molar quantity, in a reaction inert solvent such as $CH_2Cl_2$ at 0°–50° C. (conveniently at ambient temperature). When a reactant is in the form of an acid salt, a tertiary amine (e.g., triethylamine, N-methylmorpholine) is employed in an amount sufficient to neutralize said acid.

Prior to the next coupling step the α-amino group of the basic amino acid residue is deprotected, e.g., an α-Boc group is readily removed by the action of 3.5 to 4.5N HCl in dioxane at −10° to 40° C., conveniently at ambient temperature; or by the action of anhydrous trifluoroacetic acid at −20° to 20° C., conveniently at about 0°–5° C. When the carboxyl group of the compound (IX) has been protected by benzyl, hydrogenolysis is preferred for removal of the protecting group. When the carboxyl group is protected as an ester, hydrolysis is selected for removal of the protecting group.

Alternatively, the oligopeptide portion can be synthesized using solid phase peptide synthesis and can be attached to the compound of formula (IX) wherein R" is hydrogen.

The compound of formula (IX) is converted to an amide of formula (X). In a preferred method for preparing the amide, the acid of formula (IX) is reacted with dimethyl-hydroxylamine in the presence of methylchloroformate to provide the amide of formula (X). In carrying out this method the acid (IX) in a suitable solvent is contacted with an equimolar amount of methylchloroformate in the presence of a base such as 1-methylpiperidine at a temperature of from about −25° to 10° C. Suitable solvents for this reaction include tetrahydrofuran, 1,2-dimethoxyethane, and diethyleneglycol dimethylether. Subsequently, an equimolar amount of dimethylhydroxylamine is added to the reaction mixture, and the reaction is allowed to continue at ambient temperature. Under the preferred conditions mentioned above, the reaction is ordinarily complete in one to two hours. Upon completion of the reaction, the product is isolated by standard methods, for example, by extraction with a water immiscible solvent. Purification can be done by chromatography or by recrystallization from an appropriate solvent.

In a modification of this method the compound of formula (IX) can be transformed to an amide analog having a piperidinyl group in place of dimethylamino. See, for example, Husson H-P, *Tetrahedron Lett.*, 1971, 2697.

The amide is then reacted with excess of alkyl lithium wherein the alkyl is $C_1$–$C_5$. The reaction is carried out in a reaction-inert solvent at a temperature of from about −78° to about 0° C. Preferred solvents include tetrahydrofuran, 1,2-dimethoxyethane, and diethyleneglycol dimethylether. Reaction is normally complete in one to two hours. Upon completion of the reaction, the product is isolated by standard methods, for example, by extraction with a water immiscible solvent. Purification can be done by chromatography or by recrystallization from an appropriate solvent. In a modification of this method a Grignard reagent, RMgX wherein R is $C_1$–$C_5$ alkyl and X is halo, may be used to provide the compound of formula (VII). See, for example, Comins, D. I., et al., *J. Org. Chem.* 1986, 51, 3566.

The synthesis of the compounds of formula (IV A) and (IV B) is schematically depicted below:

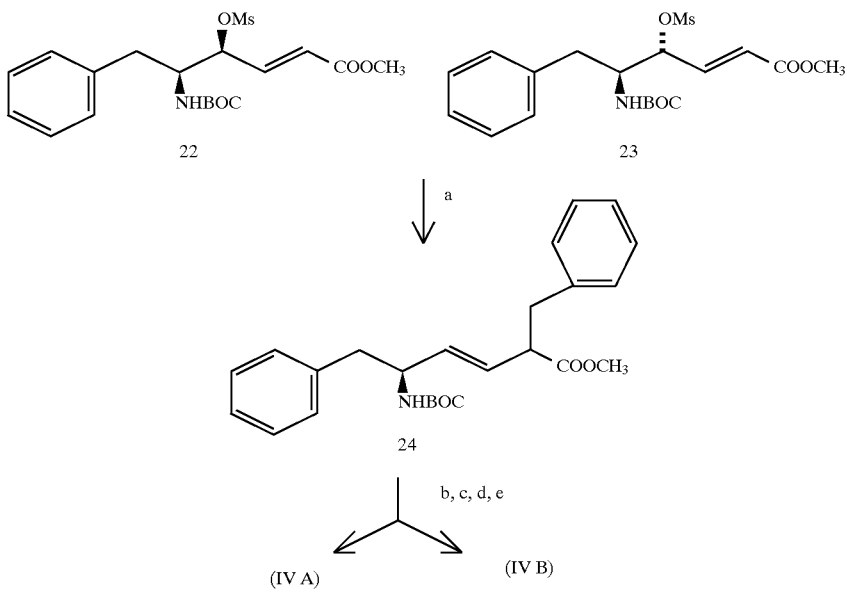

Conditions: (a) Benzyl Cu (CN) Mg Cl, BF$_3$; (b) B$_2$H$_6$; (c) H$_2$O$_2$, OH; (d) Ph$_3$P=CH$_2$; (e) MCPBA.

The compounds of the present invention contain an epoxide functionality at a strategic position such that it replaces the hydroxyl group of hydroxyethylene isosteres. The activity of the compounds of the present invention as inhibitors of HIV-1 PR is determined by studying their ability to inhibit the HIV substrate-cleaving activity of HIV protease.

The compounds of the present invention can be administered as HIV-1 protease inhibiting agent by either the oral or parental routes of administration.

Where gastrointestinal absorption permits, oral administration is preferred for reasons of patient convenience and comfort. In general, these HIV-1 PR-inhibiting compounds are normally administered in dosages ranging from about 0.1 mg to about 10 mg per kg of body weight per day; variations will necessarily occur depending upon the condition of the subject being treated and the particular compound being administered. Typically, treatment is commenced at a low daily dosage and increased by the physician only if necessary. It is to be noted that these compounds may be administered in combination with pharmaceutically acceptable carriers by either of the routes previously indicated, and that such administration can be carried out in both single and multiple dosages.

For parenteral use, the present compounds are formulated according to the known art using suitable dispersing or wetting agents and suspending agents. The sterile injectable formulation can also be a solution of suspension in a non-toxic parenterally acceptable diluent or solvent, for example, as a solution in 1,3-butandiol. Among the acceptable vehicles and solvents are water, Ringer's solution and isotonic NaCl solution, fixed oils including synthetic mono- or di-glycerides, fatty acids such as oleic acids, and mixtures thereof.

For oral administration, a wide variety of dosage forms are used, e.g., tablets, capsules, lozenges, trochees, hard candies, powders, sprays, aqueous suspension, elixirs, syrups, and the like formulated with various pharmaceutically-acceptable inert carriers. Such carriers include solid diluents or fillers, sterile aqueous media and various non-toxic organic solvents, etc. In general, the compounds of the present invention are present in such oral dosage forms at concentration levels ranging from about 0.5% to about 90% by weight of the total composition, in amounts which are sufficient to provide the desired unit dosage. Tablets may contain various excipients such as sodium citrate, calcium carbonate and calcium phosphate, along with various disintegrants such as starch (preferably potato or tapioca starch), alginic acid and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in soft and hard-filled gelatin capsules; preferred materials in this connection would also include lactose or milk sugar as well as high molecular weight polyethylene glycols. When aqueous suspensions and/or elixirs are desired for oral administration, the essential active ingredient therein may be combined with various sweetening or flavoring agents, coloring matter or dyes and, if so desired, emulsifying and/or suspending agents, together with such diluents as water, ethanol, propylene glycol, glycerin and various like combinations thereof.

The active compounds can also be administered in the form of liposomes. As is known in the art, liposomes are generally derived from phospholipids or other lipid substances. Liposomes are formed by mono-or multi-lamellar hydrated liquid crystals that are dispersed in an aqueous medium. Any non-toxic, pharmaceutically acceptable and metabolizable lipid capable of forming liposomes can be used. The present compositions in liposome form can contain stabilizers, preservatives, excipients, and the like in addition to the agent. The preferred lipids are the phospholipids and the phosphatidyl cholines (lecithins), both natural and synthetic.

Methods of forming liposomes are known in the art. See, for example, *Methods in Cell Biology*; Prescott, Ed.; Academic: New York, 1976; Vol. XIV.

Additional pharmaceutical methods may be employed to control the duration of pharmacological action. Controlled release preparations may be achieved by the use of polymers to complex or adsorb the present active compounds. The controlled delivery may be exercised by selecting appropriate macromolecules (for example, polyesters, polyamino acids, polyvinyl pyrrolidone, ethylenevinylacetate, methylcellulose, carboxymethylcellulose, and protamine sulfate) and the concentration of macromolecules as well as the methods of incorporation in order to control release. Another possible method to control the duration of action by controlled release preparations is to incorporate the active compound into particles of a polymeric material such as polyesters, polyamino acids, hydrogels, poly (lactic acid) or ethylene vinylacetate copolymers. Alternatively, instead of incorporating the active compounds into these polymeric particles, it is possible to entrap the active compounds in microcapsules prepared, for example, by coacervation techniques or by interfacial polymerization, for example, hydroxymethylcellulose or gelatin-microcapsules and poly (methylmethacrylate) microcapsules, respectively, or in colloidal drug delivery systems, for example, liposomes, albumin microspheres, microemulsions, nanoparticles, and nanocapsules or in macroemulsions. Such teachings are disclosed in *Remington's Pharmaceutical Science*, A. Oslo, Ed.; 17th ed.; Mack: Easton, Pa., 1985.

Where in vitro HIV-1 PR inhibition is desired, a compound of this invention can be utilized in an amount sufficient to provide a concentration of about 0.01 to about 2,000 manomolar (nM) with enzyme concentration of about 1 nM to about 1 $\mu$M, and a substrate concentration of about 10 to about 2,000 micromolar ($\mu$M). The amounts of enzyme, substrate and inhibitor used are largely a function of convenience, with the substrate typically being in large excess over the enzyme (e.g., 100–10,000 fold excess).

All structural designations of stereochemistry shown herein represent absolute stereochemistry. The present invention is illustrated by the following examples. However, it should be understood that the invention is not limited to the details of these examples. Proton nuclear magnetic resonance spectra (NMR) were measured at 400 MHz unless otherwise indicated for solutions in deuterochloroform ($CDCl_3$) and peak positions are expressed in parts per million (ppm) downfield from tetramethylsilane. The peak shapes are denoted as follows: s, singlet; d, doublet; t, triplet; q, quartet; m, multiplet; and b, broad.

EXAMPLE 1

HIV-1 PR INHIBITION

Typical reactions were carried out at room temperature (25° C.) in 150 $\mu$l total volumes of 100 mM MES buffer, pH 6.2, containing 1 mM ethylenediaminetetraacetic acid (EDTA) and 2 mM dithiothreitol (DTT) plus 0.1 percent (v/v) Triton X-100.

Synthetic HIV-1 protease [0.5 $\mu$g, obtained from Dr. Stephen Kent of The Scripps Research Institute; see *Cell*, 1988, 54; 363–368] was first incubated in buffer with (or without) various concentrations of "inhibitor(s)" for 30 minutes at 25° C. The protease reaction was then initiated by the addition of HIV substrate IV (Bachem Bioscience Inc.) at fixed concentrations (e.g., 100 mg/ml). HIV Substrate IV has the sequence Lys-Ala-Arg-Val-Nle-p-NO$_2$Phe-glu-Ala-Nle-NH$_2$ (SEQ ID NO 15)

At three appropriate times (normally 40, 80 and 120 minutes) the hydrolysis was stopped by adding a 40 $\mu$l aliquot from the reaction to 40 $\mu$l of a prepared quench solution. The quench solution was 1:4 acetonitrile:water (3 percent trifluoroacetic acid; TFA) and contained 150 $\mu$M m-toluic acid which served as an HPLC standard. Quenched aliquots were injected into a reversed-phase HPLC (Hitachi Instrument; VYDAC $C_{18}$ column No. 201TP54) and eluted with an isocratic mixture of 20 percent acetonitrile/80 percent water (0.1 percent TFA) flowing at 2.0 m./min. Reaction progress was monitored by following the increasing absorbance (peak height) of the substrate IV cleavage product detected at 254 nM.

Determination of kinetic constants was done with the program KinetAsyst (IntelliKinetics). In FIG. 1, $v_0$ and $v_1$ represent velocity with or without inhibitor (the compound of Example 2), respectively.

Semilogarithmic plot of protease activity remaining after preincubation at the indicated times with 2 mM of the inhibitor is provided in FIG. 1.

Inhibition of HIV-1 PR by the tested compound shows competitive and timedependent inactivation of the protease with t½ being 3 hr. at 2 mM.

EXAMPLE 2

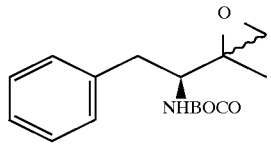

A 10 ml round bottom flask containing a magnetic stirring bar was charged with NaH (40 mg of dispersion washed in situ with 3×3 ml hexane; 0.84 mmol) and DMSO (0.5 ml). This was hewed in an oil bath at 70° C. for 1 hour. After cooling to room temperature, THF (1.2 ml) was added and the grayish solution cooled in an ice bath. The mixture was stirred vigorously and the trimethylsulfonium iodide (0.84 mmol, 175 mg) in DMSO (0.7 ml) was added via Hamilton syringe beneath the surface of the solution. After 5 minutes, the ketone (0.7 mmol, 184 mg) in THF (0.7 ml) was added via syringe beneath the surface of the solution. An opaque, light yellow mixture developed immediately. After 30 minutes in the ice bath, brine (5 ml) was added to the cold, stirring mixture. This was then diluted with 40 ml EtOAc and washed with brine (5×10 ml), dried with $Na_2SO_4$ and the solvent removed on a rotary evaporator leaving an oil. A portion was purified via prep TLC (full plates) affording a white, crystalline solid (estimated total yield: 120 mg, 60%).

$^{13}$C NMR (d$_6$-DMSO) δ 155.32, 155.27; 138.92, 138.82; 129.05,128.92; 128.00, 127.95; 125.91; 77.64; 77.55; 58.26, 58.00; 56.71, 56.03; 52.70, 51.46; 36.09, 35.64; 28.16; 18.15; 16.92.

$^{1}$H NMR: 64:36 Diastereomeric ratio δ 7.35–7.15 (m, 10H), 4.45 (brd, 2H), 4.05 (brs, 1H), 3.75 (br s, 1H), 3.1–2.75 (m, 4H), 2.7–2.5 (m, 4H), 1.45 (S, 3H), 1.35 (3, 3H), 1.3 (S, 9H), 1.28 (S, 9H).

PREPARATION 1

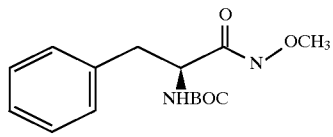

A 250 ml round bottom flask containing a magnetic stirring bar was charged with l-phenylalanine (BOC protected) amino acid (4 g, 15.1 mmol) and THF (60 ml).

The solution was cooled in an ice bath and 1-Me-piperidine (15.1 mmol, 1.5 g, 1.85 ml) was added. To this solution was then added methylchloroformate (15.1 mmol, 1.43 g, 1.2 ml). A thick white precipitate developed immediately. After 10 minutes, diemthylhydroxylamine (15.1 mmol, 1.5 g) was added followed by 1-Me-piperidine (30.2 mmol, 3.7 ml). After stirring 3 hours at room temperature, the mixture was diluted with EtOAc (200 ml) and washed with 5% HCl (4×50 ml), 5% NaHCO$_3$ (5×50 ml), and brine (2×50 ml), dried with Na$_2$SO$_4$, filtered, 10 g silica gel added and the solvent removed on a rotary evaporator. The preadsorbed product was purified via flash chromatography [5×14 cm 50/50 EtOAc/HEX product at 280–500 ml] affording a pasty, white solid (1.3 g, 28%).

PREPARATION 2

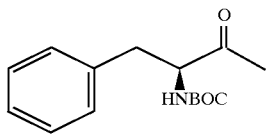

A 100 ml round bottom flask containing a magnetic stirring bar was charged with the amide (1.24 g, 4 mmol) and THF (30 ml). The solution was cooled to −78° C. in a dry ice-acetone bath. The MeLi (7 ml of 1.4M ether solution, 10 mmol) was then added via syringe. The dry ice bath was replaced by an ice bath and the clear, virtually colorless solution stirred for 1 hour. The ice cold solution was poured into 100 ml of ice cold 5% citric acid and extracted with EtOAc (150 ml), washed with 5% citric acid (1×20 ml), brine (2×20 ml), dried with Na$_2$SO$_4$, filtered, and the solvent removed on a rotary evaporator and then vacuum pump according a light yellow oil which solidified to a pale yellow, waxy crystalline solid (98 mg, 82%). This material was pure by NMR and TLC.

$^1$H NMR: δ 7.35–7.10 (m, 5H), 5.10 (br d, 1H), 4.55 (dd, 1H), 3.05 (ddd, 2H), 2.15 (s, 3H), 1.35 (s, 9H).

The invention now being fully described, it will be apparent to one of ordinary skill in the art that many changes and modifications can be made without departing from the spirit or scope of the invention.

EXAMPLE 3 for Compound Class (VI-B)

Figure 2:
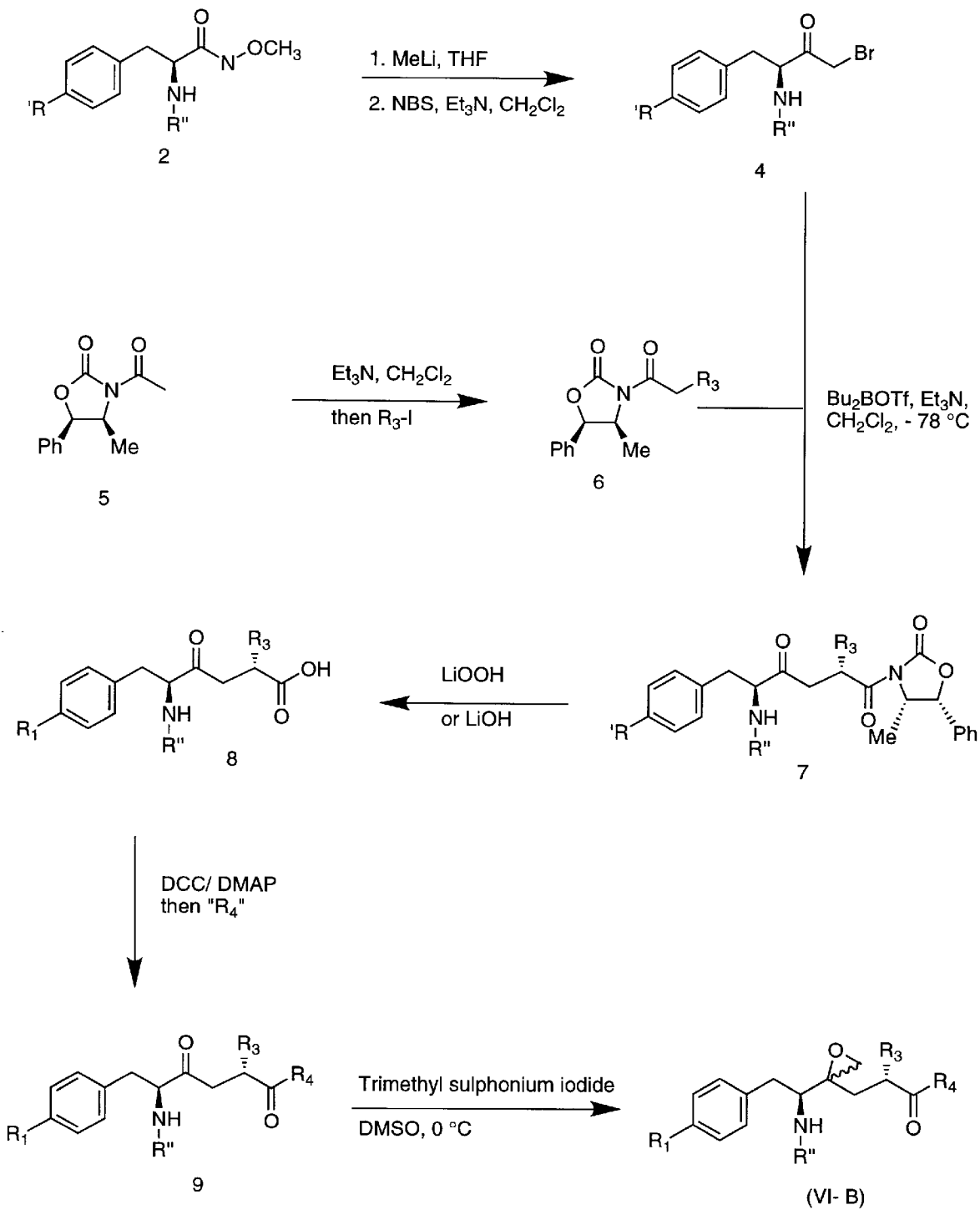
FIG. 2 illustrates the synthesis of compound class (VI-B).

Synthesis of compound 4 (FIG. 2)

1.0 equivalent of compound 3 is suspended in 0.10M methylene chloride and cooled to 0° C. Triethylamine (2.0 equivalents) is next added, followed by 1.1 equivalents of N-bromosuccinamide (NBS). The reaction mixture is allowed to stir for 1 hour at 0° C. and is then diluted with diethyl ether and and quenched with a saturated solution of ammonium acetate. The reaction mixture is extracted with water, brine and then dried over magnesium sulfate. Solvent is then removed on a rotary evaporator and product is filtered and purified by flash chromatography.

Synthesis of compound 6 (FIG. 2)

1.0 equivalent of compound 5 (Synthesized according to the conditions in Evans et al. *J. Am. Chem. Soc.* Vol. 112, No 19, 1990) is suspended in 0.10M methylene chloride and cooled to 0° C. Triethylamine (2.0 equivalents) is next added, followed by 1.1 equivalents of R$_3$-I (R$_3$-I is an iodide derivative where R$_3$=C$_1$–C$_5$ alkyl, C$_7$–C$_9$ phenylalkyl, C$_{11}$–C$_{13}$ naphthylalkyl or C$_8$–C$_{10}$phenylalkenyl; R$_3$-I is prepared via standard iodination conditions on a hydroxyl moiety using iodine, triphenylphosphine, methylene chloride). The reaction mixture is allowed to stir for 12 hours at 0° C. and is then diluted with diethyl ether and and quenched with a saturated solution of ammonium acetate. The reaction mixture is extracted with water, brine and then dried over magnesium sulfate. Solvent is then removed on a rotary evaporator and product is filtered and purified by flash chromatography.

Synthesis of compound 7 (FIG. 2)

1.0 equivalents of compound 6 is suspended in 0.10M methylene chloride and cooled to −15° C. Next, 1.1 equivalents of di-n-butylboron triflate (Aldrich in 1.0M methylene chloride) followed by 1.5 equivalents of triethylamine is added and allowed to stir for 15 minutes. The solution is then cooled to −78° C. and 1.0 equivalents of compound 4 (vida supra) is added in 2M methylene chloride via cannula. The resulting pale yellow solution is stirred at −78° C. for 1.5 hour, then warmed to 0° C. over 30 minutes and stirred for 30 minutes. The reaction is quenched by the addition of 1.0M pH 7 phosphate buffer, followed by 1.0M methanol added dropwise over 30 minutes at 0° C. The reaction mixture is then diluted with diethyl ether and and quenched with a saturated solution of ammonium acetate. The reaction mixture is extracted with water, brine and then dried over magnesium sulfate. Solvent is then removed on a rotary evaporator and product is filtered and purified by flash chromatography.

Synthesis of compound 8 (FIG. 2)

1.0 equivalent of compound 7 is stirred in 0.10M tetrahydrofuran (THF) and 1.0M water, cooled to 0° C. and treated with 4 equivalents of 31% hydrogen peroxide, followed by 2 equivalents of solid lithium hydroxide. After stirring at 0° C. for 30 minutes, the reaction is treated with a solution of 4 equivalents of sodium sulfate in water followed by 4 equivalents of sodium bicarbonate. Following removal of the THF in vacuo, the reaction mixture is then diluted with diethyl ether and and quenched with a saturated solution of ammonium acetate. The reaction mixture is extracted with water, brine and then dried over magnesium sulfate. Solvent is then removed on a rotary evaporator and product is filtered and purified by flash chromatography.

Synthesis of compound 9 (FIG. 2)

1.0 equivalent of compound 8 is suspended in 0.10M solution of methylene chloride, cooled to 0° C. and treated with 2.0 equivalents of DCC (dicyclohexylcarbodiimide in 1.0 solution methylene chloride; Aldrich) followed by 0.10 equivalents of DMAP (4-dimethylaminopyridine). The mixture is then exposed to 1.0 equivalents of R$_4$—OH or R$_4$—NH$_2$ (where R$_4$ is a carboxyl protecting group, a protecting amino group or an oligopeptide containing a sequence of up to four amino acid residues with a C-terminating group; each synthesized by standard peptide procedures disclosed supra or commercially available) and allowed to stir for up to 12 hours at 0° C. and is then diluted with diethyl ether and and quenched with a saturated solution of ammonium acetate. The reaction mixture is extracted with water, brine and then dried over magnesium sulfate. Solvent is then removed on a rotary evaporator and product is filtered and purified by flash chromatography.

Synthesis of compound class (VI-B)(FIG. 2)

A 10 ml round bottom flask containing a magnetic stirring bar is charged with NaH (40 mg of dispersion washed in situ with 3×3 ml hexane; 0.84 mmol) and DMSO (0.5 ml). this is heated in an oil bath at 70° C. for 1 hour. After cooling to room temperature, THF (1.2 ml) is added and the grayish solution is cooled in an ice bath. The mixture is stirred vigorously and the trmethylsulfonium iodide (0.84 mmol, 175 mg) in DMSO (0.7 ml) is added via syringe beneath the surface of the solution. After 5 minutes, the ketone, compound 9, (0.7 mmol) in THF (0.7 ml) is added via syring benath the surface of the solution. After 30 minutes, in the ice bathe, brine (5 ml) is added to the cold, stirring mixture. This is then diluted with 40 ml ethylacetate and washed with brine (5×10 ml) dried with sodium sulfate and the solvent is removed on a rotary evaporator leaving an oil. Product is filtered and purified by flash chromatography.

EXAMPLE 4 for Compound Class (VI-C)

Figure 3:
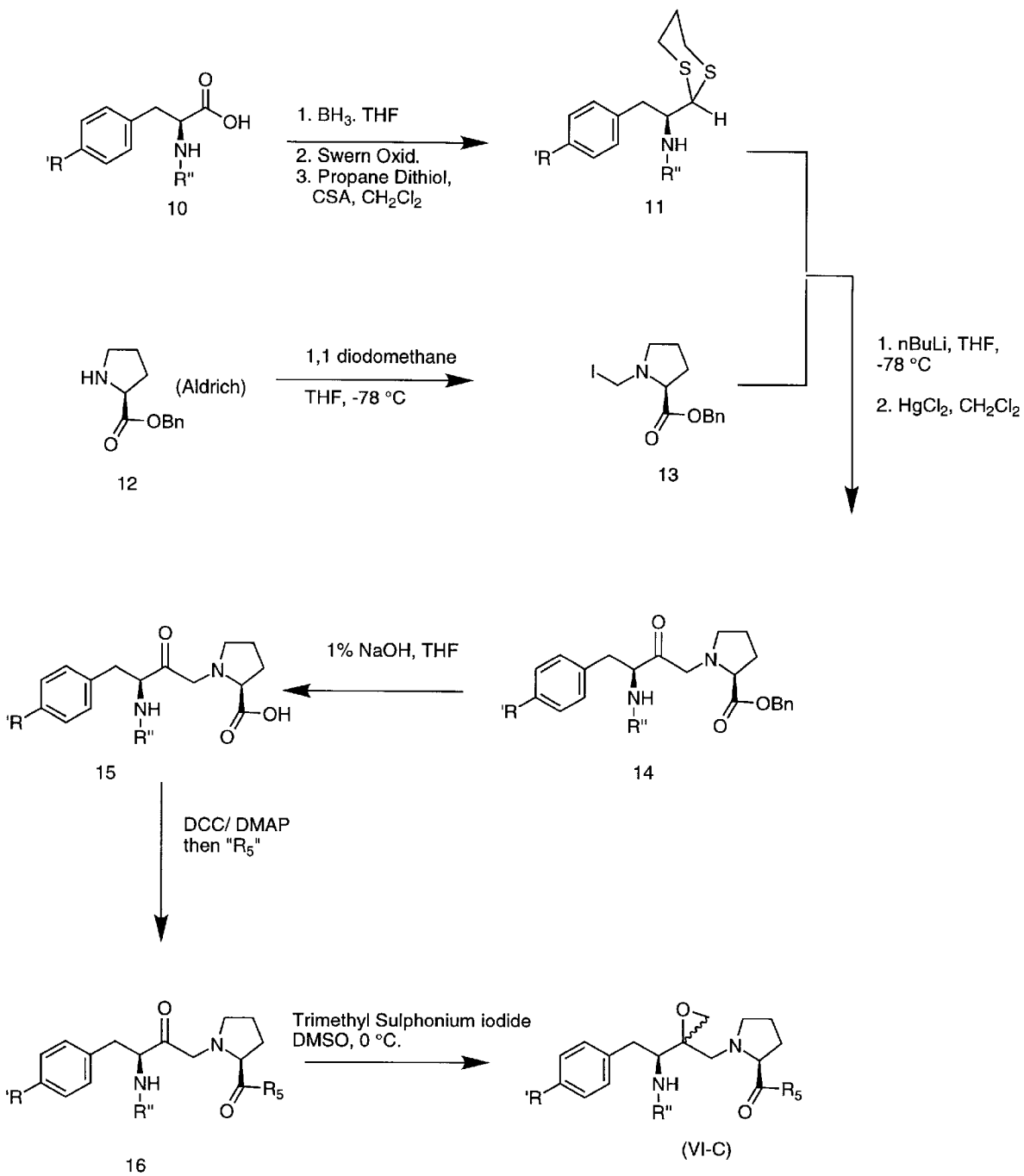
FIG. 3 illustrates the synthesis of compound class (VI-C).

Synthesis of compound 10 (FIG. 3)

Either phenylalanine where R'=H or Tyrosine where R'=OH (or protected hydroxyl) is N-protected via standard conditions with R" where R" is an amino protecting group including acetyl, BOC, 9-Fluorocene, etc. Alternatively, R" is an oligopeptide confining sequence of up to four amino acid residues with an N-terminating group, sequenced using standard peptide conditions (vida supra). The oligopeptide can be coupled to the amino group on compound 10 using standard conditions which may include DCC (dicyclohexylcarbodiimide in 1.0 solution methylene chloride; Aldrich) followed by 0.10 equivalents of DMAP (4-dimethylaminopyridine). The mixture is then exposed to 2.0–5.0 equivalents of R"—COOH (where R" is an oligopeptide confining sequence of up to four amino acid residues with an N-terminating group-added in excess) and allowed to stir for up to 12 hours at 0° C. and is then diluted with diethyl ether and and quenched with a saturated solution of ammonium acetate. The reaction mixture is extracted with water, brine and then dried over magnesium sulfate. Solvent is then removed on a rotary evaporator and product is filtered and purified by flash chromatography.

Synthesis of compound 11 (FIG. 3)

Compound 10 is suspended in 0.10M THF, cooled to 0° C. and exposed to 1.1 equivalent Borane-THF (Aldrich; 1M solution added dropwise). The mixture is allowed to stir at 0° C. for 1 hour and then quenched by the addition of 0.10M methanol after stiring for an additional 30 minutes. The mixture is then diluted with diethyl ether and and quenched with a saturated solution of ammonium acetate. The reaction mixture is extracted with water, brine and then dried over magnesium sulfate. Solvent is then removed on a rotary evaporator and product is filtered and purified by flash chromatography.

The resulting alcohol is then oxidized to the aldehyde using standard Swern oxidation conditions as follows. To a cooled (−78° C. stirred solution of 1.1 equivalents of oxalyl chloride in methylene chloride (0.10M) is added (1.1 equivalents of DMSO drowise over a 2 minute period. After an additional 5 minutes, this solution is added via cannula to a cooled (−78° C.) stirred solution of 1.0 equivalents of alcohol in 0.10M methylene chloride. The resulting mixture is maintained at −78° C. for 20 min, 1.1 equivalents of triethylamine is added and then allowed to rise to 0° C. The solution is diluted with 20% methylene chloride/hexane and extracted with 10% aqueous sodium bisulfate, water, brine and then dried over magnesium sulfate. Solvent is then removed on a rotary evaporator and product is filtered and purified by flash chromatography.

The aldehyde is then oxidized to the dithiane by suspending the aldehyde in 0.10M methylene chloride, cooling to 0° C., adding 0.10 equivalents of camphorsulphonic acid (CSA; Aldrich) followed by 1.1 equivalents of propane dithiol. The mixture is allowed to stir for 1.0 hour or until comple and the solution is diluted with 20% methylene chloride/hexane and extracted with 10% aqueous sodium bisulfate, water, brine and then dried over magnesium sulfate. Solvent is then removed on a rotary evaporator and product is filtered and purified by flash chromatography to provide the dithiane compound 11.

Synthesis of compound 13 (FIG. 3)

1.0 equivalents of compound 12, commercially available from Aldrich, is exposed to 1.1 equivalents 1,1 diiodomethane at −78° C. in THF. The mixture is stirred for 1 hour and is diluted with ether and extracted with 10% aqueous sodium bisulfate, water, brine and then dried over magnesium sulfate. Solvent is then removed on a rotary evaporator and product is filtered and purified by flash chromatography to provide the iodide compound 13.

Synthesis of compound 14 (FIG. 3)

1.0 equivalent of compound 11 is suspended in 0.10M THF, cooled to −78° C. and exposed to 1.1 equivalents of a 2.0M solution of n-BuLi in THF. The resulting red slurry is stirred for 15 minutes and then 1.0 equivalents of the iodide 13 (vida supra) is added dropwise (via cannula) in a 1.0M solution of THF, cooled to −78° C. The mixture is then stirred for 6–12 hours, allowing to warm to 0° C. The product is diluted with ether and extracted with 10% aqueous sodium bisulfate, water, brine and then dried over magnesium sulfate. Solvent is then removed on a rotary evaporator and product is filtered and purified by flash chromatography.

The coupled dithiane compound is then resuspended in 0.10M methylene chloride, cooled to 0° C. and then 1.1 equivalents of $HgCl_2$ is added and the mixture is allowed to stir for 1 hour. The product is then diluted with ether and extracted with 10% aqueous sodium bisulfate, water, brine and then dried over magnesium sulfate. Solvent is then removed on a rotary evaporator and product is filtered and purified by flash chromatography to provide the coupled product 14.

Synthesis of compound 15 (FIG. 3)

1.0 equivalent of compound 14 is stirred in 0.10M tetrahydrofuran (THF) and 1.0M water, cooled to 0° C. and treated with 4 equivalents 1% sodium hydroxide. After stirring at 0° C. for 30 minutes, the reaction is treated with a solution of 4 equivalents of sodium sulfate in water followed by 4 equivalents of sodium bicarbonate. Following removal of the THF in vacuo, the reaction mixture is then diluted with diethyl ether and and quenched with a saturated solution of ammonium acetate. The reaction mixture is extracted with water, brine and then dried over magnesium sulfate. Solvent is then removed on a rotary evaporator and product is filtered and purified by flash chromatography.

Synthesis of compound 16 (FIG. 3)

1.0 equivalent of compound 15 is suspended in 0.10M solution of methylene chloride, cooled to 0° C. and treated with 2.0 equivalents of DCC (dicyclohexylcarbodiimide in 1.0 solution methylene chloride; Aldrich) followed by 0.10 equivalents of DMAP (4-dimethylaminopyridine). The mixture is then exposed to 1.0 equivalents of $R_5$—OH or $R_5$—$NH_2$ (where $R_5$ is a carboxyl protecting group, a protecting amino group or an oligopeptide containing a sequence of up to four amino acid residues with a C-terminating group; each synthesized by standard peptide procedures disclosed supra or commercially available) and allowed to stir for up to 12 hours at 0° C. and is then diluted with diethyl ether and and quenched with a saturated solution of ammonium acetate. The reaction mixture is extracted with water, brine and then dried over magnesium sulfate. Solvent is then removed on a rotary evaporator and product is filtered and purified by flash chromatography.

Synthesis for compound class (VI-C) (FIG. 3)

A 10 ml round bottom flask containing a magnetic stirring bar is charged with NaH (40 mg of dispersion washed in situ with 3×3 ml hexane; 0.84 mmol) and DMSO (0.5 ml). this is heated in an oil bath at 70° C. for 1 hour. After cooling to room temperature, THF (1.2 ml) is added and the grayish solution is cooled in an ice bath. The mixture is stirred vigorously and the trmethylsulfonium iodide (0.84 mmol, 175 mg) in DMSO (0.7 ml) is added via syringe beneath the surface of the solution. After 5 minutes, the ketone, compound 16, (0.7 mmol) in THF (0.7 ml) is added via syring benath the surface of the solution. After 30 minutes, in the ice bath, brine (5 ml) is added to the cold, stirring mixture. This is then diluted with 40 ml ethylacetate and washed with brine (5×10 ml) dried with sodium sulfate and the solvent is removed on a rotary evaporator leaving an oil. Product is filtered and purified by flash chromatography.

EXAMPLE 5 for Compound Class (VI-D)

Figure 4:
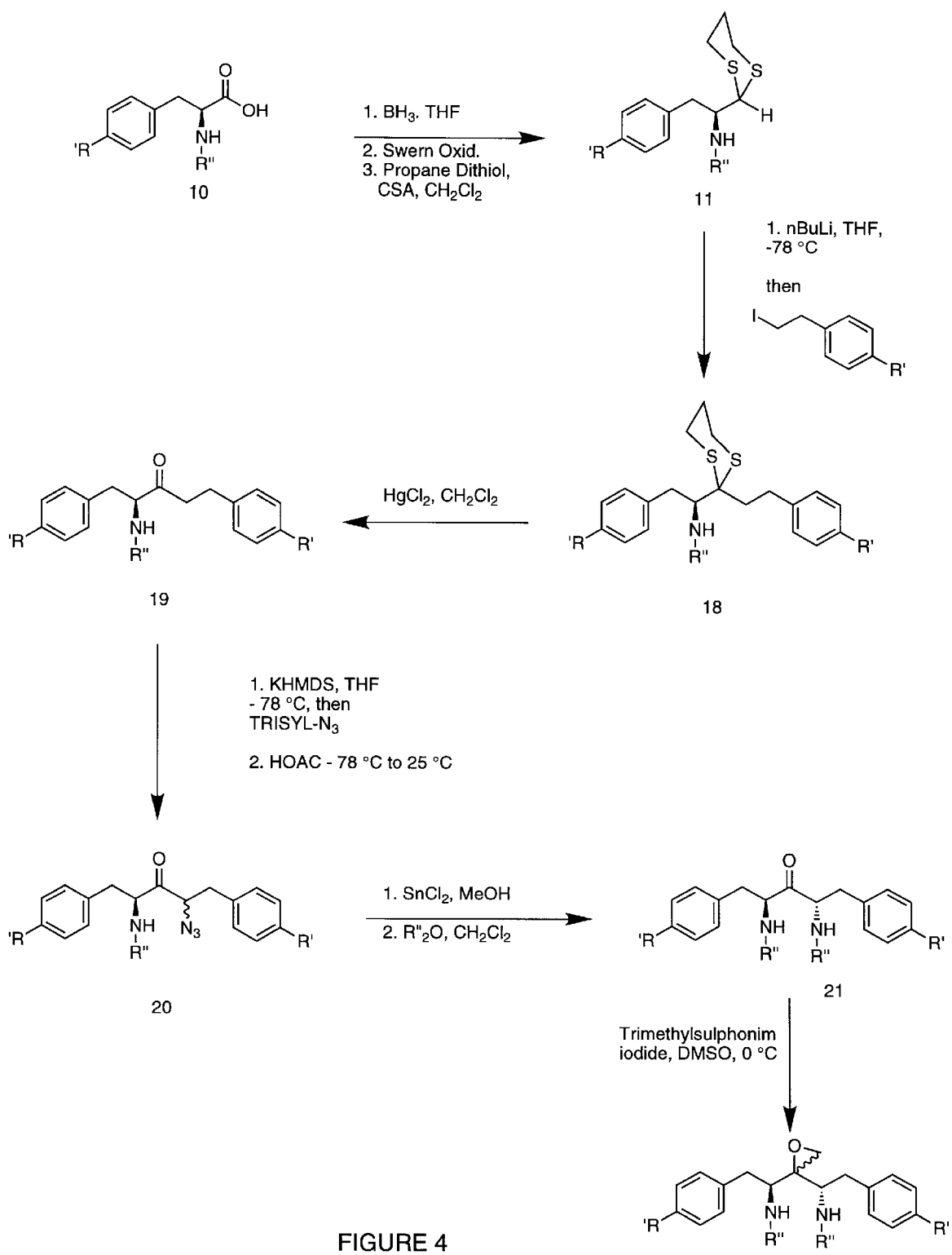
FIG. 4 illustrates the synthesis of compound class (VI-D).

Synthesis of compound 18 (FIG. 4)

1.0 equivalent of compound 11 is suspended in 0.10M THF, cooled to −78° C. and exposed to 1.1 equivalents of a 2.0M solution of n-BuLi in THF. The resulting red slurry is stirred for 15 minutes and then 1.0 equivalents of the iodide 17 (commercially available where R'=H, hydroxy, or can be protected hydroxy) is added dropwise (via cannula) in a 1.0M solution of THF, cooled to −78° C. The mixture is then stirred for 6–12 hours, allowing to warm to 0° C. The product is diluted with ether and extracted with 10% aqueous sodium bisulfate, water, brine and then dried over magnesium sulfate. Solvent is then removed on a rotary evaporator and product is filtered and purified by flash chromatography to provide the coupled dithiane product 18.

Synthesis of compound 19 (FIG. 4)

The coupled dithiane compound is then resuspended in 0.10M methylene chloride, cooled to 0° C. and then 1.1 equivalents of $HgCl_2$ is added and the mixture is allowed to stir for 1 hour. The product is then diluted with ether and extracted with 10% aqueous sodium bisulfate, water, brine and then dried over magnesium sulfate. Solvent is then removed on a rotary evaporator and product is filtered and purified by flash chromatography to provide the deprotected coupled product 19.

Synthesis of compound 20 (FIG. 4)

Procedure adapted from Evans et al. JACS, vol 112, 1990, 4023. To 0.10M THF stirred at −78° C. under nitrogen, was added 1.1 equivalents of potassium hexamethyidisilazide (KHMDS) (0.48M in toluene). To the resulting soultion is added via cannula a preccoled (−78° C.) solution of 1.0 equivalents of compound 19 in 1M dry THF. To the above solution of potassium enolate, stirred at −78° C., is added via cannulation a precooled (−78° C.) solution of 1.23–1.26 equivalents of trisyl azide (Harmon et al JOC 1973, 38,11–16) in 1.0M THF. After 1–2 min, the reaction was quenched with 4.5 equivalents of glacial acetic acid. The cooling bath is removed, and the reaction is stirred at room temperature for 10–12 hours. The solution is partitioned between methylene chloride (40 mL) and dilute brine (40 mL). The product is then diluted with ether and extracted with 10% aqueous sodium bisulfate, water, brine and then dried over magnesium sulfate. Solvent is then removed on a rotary evaporator and product is filtered and purified by flash chromatography to provide the deprotected coupled product 20.

Synthesis of compound 21 (FIG. 4)

Procedure adapted from Evans et al. JACS, vol 112, 1990, 4029. A 500 mL flame-dried round-bottom flask is charged with 0.10M of anhydrous methanol followed by 2 equiv of $SnCl_2$ (Aldrich). The flask is swept with nitrogen, stirred at room temperature for 10 min, and then cooled to 0° C. Azido compound 20 (1.0 equivalents) in 1.0M of anhydrous methanol is then added via syringe, stirred at 0° C. for 5 minutes and then allowed to warm to room temperature for an additional 2 h. The methanol is then removed in vacuo to yield a light yellow-cream colored foam. To this foam is added 0.10M dioxane, followed by 1.5 equivalents of $R''_2O$ (where $R''_2O$ can be $BOC_2O$, or any amino protecting group or where R" is an oligopeptide contining sequence of up to four amino acid residues with an N-terminating group-added in excess). The product is then diluted with ether and extracted with 10% aqueous sodium bisulfate, water, brine and then dried over magnesium sulfate. Solvent is then removed on a rotary evaporator and product is filtered and purified by flash chromatography to provide the deprotected coupled product 21.

Synthesis for compound class (VI-D) (FIG. 4)

A 10 ml round bottom flask containing a magnetic stirring bar is charged with NaH (40 mg of dispersion washed in situ with 3×3 ml hexane; 0.84 mmol) and DMSO (0.5 ml). this is heated in an oil bath at 70° C. for 1 hour. After cooling to room temperature, THF (1.2 ml) is added and the grayish solution is cooled in an ice bath. The mixture is stirred vigorously and the trmethylsulfonium iodide (0.84 mmol, 175 mg) in DMSO (0.7 ml) is added via syringe beneath the surface of the solution. After 5 minutes, the ketone, compound 21, (0.7 mmol) in THF (0.7 ml) is added via syring benath the surface of the solution. After 30 minutes, in the ice bath, brine (5 ml) is added to the cold, stirring mixture. This is then diluted with 40 ml ethylacetate and washed with brine (5×10 ml) dried with sodium sulfate and the solvent is removed on a rotary evaporator leaving an oil. Product is filtered and purified by flash chromatography.

EXAMPLE 6 FOR COMPOUND CLASS (IVA AND IVB)

Synthesis of compound 22 and compound 23

Compound 10 is suspended in 0.10M THF, cooled to 0° C. and exposed to 1.1 equivalent Borane-THF (Aldrich; 1M solution added dropwise). The mixture is allowed to stir at 0° C. for 1 hour and then quenched by the addition of 0.10M methanol after stiring for an additional 30 minutes. The mixture is then diluted with diethyl ether and and quenched with a saturated solution of ammonium acetate. The reaction mixture is extracted with water, brine and then dried over magnesium sulfate. Solvent is then removed on a rotary evaporator and product is filtered and purified by flash chromatography.

The resulting alcohol is then oxidized to the aldehyde using standard Swern oxidation conditions as follows. To a cooled (−78° C. stirred solution of 1.1 equivalents of oxalyl chloride in methylene chloride (0.10M) is added (1.1 equivalents of DMSO drowise over a 2 minute period. After an additional 5 minutes, this solution is added via cannula to a cooled (−78° C.) stirred solution of 1.0 equivalents of alcohol in 0.10M methylene chloride. The resulting mixture is maintained at −78° C. for 20 min, 1.1 equivalents of triethylamine is added and then allowed to rise to 0° C. The solution is diluted with 20% methylene chloride/hexane and extracted with 10% aqueous sodium bisulfate, water, brine and then dried over magnesium sulfate. Solvent is then removed on a rotary evaporator and product is filtered and purified by flash chromatography to afford the aldehyde.

1.1 equivalents of organostanane, Sn—$CHCHCOOCH_3$, as prepared in Marshall et al. ChemTracts March/April 1992, 75 is added dropwise via cannulla at −78° C. in a THF solution to the above formed aldehyde (1.0 equivalents) in 0.10 Molar THF at −78° C. The resulting mixture is maintained at −78° C. for 20 min and then allowed to rise to 0° C. The solution is quenched with 1.1 equivalents mesylchloride (Aldrich), stirred for an additional 1 hour at 0° C. and then diluted with ether and extracted with 10% aqueous sodium bisulfate, water, brine and then dried over magnesium sulfate. Solvent is then removed on a rotary evaporator and product is filtered and purified by flash chromatography to afford the compounds 22 and 23.

Synthesis of compound 24

Compound mixture 22 and 23 are suspended in 0.10M methylene chloride, cooled to −78° C. and 1.1 equivalents of Benzyl Cu(CN) Mg Cl (House et. al. Journal of Organic Chemistry 1975, 40, 10) are added dropwise via cannula in 1.0M methylene chloride. The resulting mixture is maintained at −78° C. for 20 min and then allowed to rise to 0° C. The solution is quenched with 0.10 equivalents of boron-trifluoride etherate ($BF_3$), diluted with ether and extracted with 10% aqueous sodium bisulfate, water, brine and then dried over magnesium sulfate. Solvent is then removed on a rotary evaporator and product is filtered and purified by flash chromatography to afford the compound 24.

Synthesis of compound (IVA or IVB)

Compound 24 is suspended in 0.10M THF, cooled to 0° C. and exposed to 1.1 equivalent Borane-THF (Aldrich; 1M solution added dropwise; equivalent of $B_2H_6$). The mixture is allowed to stir at 0° C. for 1 hour and then quenched by the addition of 0.10M methanol after stiring for an additional 30 minutes. The mixture is then diluted with diethyl ether and and quenched with a saturated solution of ammonium acetate. The reaction mixture is extracted with water, brine and then dried over magnesium sulfate. Solvent is then removed on a rotary evaporator and product is filtered and purified by flash chromatography to form the alcohol product.

1.0 equivalent of the above made alchol compound is stirred in 0.10M tetrahydrofuran (THF) and 1.0M water, cooled to 0° C. and treated with 4 equivalents of 31% hydrogen peroxide and 0.10 equivalent sodium hydroxide. After stirring at 0° C. for 30 minutes, the reaction is treated with a solution of 4 equivalents of sodium sulfate in water followed by 4 equivalents of sodium bicarbonate. Following removal of the THF in vacuo, the reaction mixture is then diluted with diethyl ether and and quenched with a saturated solution of ammonium acetate. The reaction mixture is extracted with water, brine and then dried over magnesium sulfate. Solvent is then removed on a rotary evaporator and product is filtered and purified by flash chromatography to form the aldehyde product.

Next 1.0 equivalents of the aldehyde are suspended in 0.10M methylene chloride and 1.2 equivalents of $Ph_3P=CH_2$ are added (commercially available from Aldrich; made up as 1.0M solution methylene chloride). The resulting soultion is stirred at 25° C. for 12 h. The reaction mixture is then diluted with diethyl ether and and quenched with a saturated solution of ammonium acetate. The reaction mixture is extracted with water, brine and then dried over magnesium sulfate. Solvent is then removed on a rotary evaporator and product is filtered and purified by flash chromatography to form the olefin product.

Finally, the epoxide products (IVA and IVB) is synthesized by suspension of the above formed olefin product (1.0 equivalents) in methylene chloride (0.10M), cooled to 0° C. and 1.1 equivalents of MCPA (2-(4-chloro-o-tolyoxy)acetic acid (Aldrich)) is added and the solution is stirred at 0° C. for 12 h. The reaction mixture is then diluted with diethyl ether and and quenched with a saturated solution of ammonium acetate. The reaction mixture is extracted with water, brine and then dried over magnesium sulfate. Solvent is then removed on a rotary evaporator and product is filtered and purified by flash chromatography to form the epoxide products (IVA and IVB).

We claim:

1. A human immunodeficiency virus protease inhibiting compound of the formula:

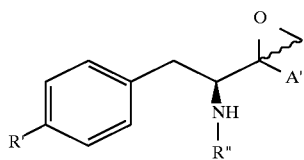

or a pharmaceutically-acceptable acid-addition salt thereof, wherein

R' is selected from a group consisting of hydrogen, hydroxyl, and a protected hydroxyl;

R" is selected from a group consisting of an amino protecting group, and U—V,
  wherein U is an oligopeptide containing a sequence of up to five amino acids and V is an N-terminating group; and A is represented by the following structure:

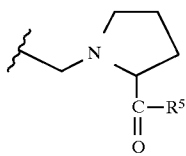

wherein $R^5$ is selected from the group consisting of $C_1$–$C_3$ alkoxy, a protected amino group, and O—Q, wherein O is an oligopeptide containing a sequence of up to four amino acid residues and Q is a C-terminating group.

2. The compound according to claim 1, wherein R' is hydrogen.

3. The compound according to claim 1, wherein R" is an amino protecting group selected from Ac, Bz, Boc, Cbz and Tba.

4. The compound according to claim 1, wherein R" is U—V.

5. The compound according to claim 4, wherein U is a sequence selected from Asn, His, Phe, Val, Ile-Thr, Ala-Ala, Phe-Phe, Val-Val, His-Phe, Ala-Ala-Ser, Asn-Leu-Ser, Asn-Gln-Ser-Val (SEQ ID NO 13), and His-Phe-Pro-His (SEQ ID NO 14).

6. The compound according to claim 4, wherein V is an N-terminating group selected from Ac, Boc, Cbz, Noa and Qc.

7. The compound according to claim 1, wherein $R^5$ is t-butoxy.

8. The compound according to claim 1, wherein $R^5$ is O—Q.

9. The compound according to claim 1, wherein $R^5$ is a sequence selected from Ile-Val and Val-Val.

10. The compound according to claim 8, wherein Q is amino or $C_1$–$C_3$ alkoxy.

* * * * *

SEQUENCE LISTING ( 1 ) GENERAL INFORMATION:

( i i i ) NUMBER OF SEQUENCES: 30

( 2 ) INFORMATION FOR SEQ ID NO:1:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: Peptide
        ( B ) LOCATION: 1
        ( D ) OTHER INFORMATION: /note= "serine is linked to CH3C(O)
            -   in formula (V A) or (V B)"

( i x ) FEATURE:
        ( A ) NAME/KEY: Peptide
        ( B ) LOCATION: 4
        ( D ) OTHER INFORMATION: /note= "Pro-Ile-Val-OCH3 is
            connected to Phe via Psi[]in formula (V A) or (V
            B)"

( x i ) SEQUENCE DESCRIPTION: SEQ ID NO:1:

Ser    Leu    Asn    Phe
    1

( 2 ) INFORMATION FOR SEQ ID NO:2:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: Peptide
        ( B ) LOCATION: 1
        ( D ) OTHER INFORMATION: /note= "serine is linked to C5H11C(O) in formula (V A) or (V B)"

( i x ) FEATURE:
        ( A ) NAME/KEY: Peptide
        ( B ) LOCATION: 4
        ( D ) OTHER INFORMATION: /note= "Pro-Ile-Val-OCH3 is connected to Phe via Psi[]in formula (V A) or (V B)"

( x i ) SEQUENCE DESCRIPTION: SEQ ID NO:2:

Ser    Leu    Asn    Phe
    1

( 2 ) INFORMATION FOR SEQ ID NO:3:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: Peptide
        ( B ) LOCATION: 1
        ( D ) OTHER INFORMATION: /note= "serine is linked to CH3C(O) in formula (V A) or (V B)"

( i x ) FEATURE:
        ( A ) NAME/KEY: Peptide
        ( B ) LOCATION: 4
        ( D ) OTHER INFORMATION: /note= "Pro-Ile Val-OCH3 is connected to Tyr via Psi[]in formula (V A) or (V B)"

( x i ) SEQUENCE DESCRIPTION: SEQ ID NO:3:

Ser    Leu    Asn    Tyr
    1

( 2 ) INFORMATION FOR SEQ ID NO:4:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: Peptide
        ( B ) LOCATION: 1
        ( D ) OTHER INFORMATION: /note= "serine is linked to CH3C(O) in formula (V A) or (V B)"

( i x ) FEATURE:
        ( A ) NAME/KEY: Peptide ( B ) LOCATION: 4
( D ) OTHER INFORMATION: /note= "PIC-NH-tBu* is connected to
Phe via Psi[]in formula (V A) or (V B)"

( x i ) SEQUENCE DESCRIPTION: SEQ ID NO:4:

Ser Leu Asn Phe
1

( 2 ) INFORMATION FOR SEQ ID NO:5:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( v ) FRAGMENT TYPE: internal ( i x ) FEATURE:
( A ) NAME/KEY: Peptide
( B ) LOCATION: 1
( D ) OTHER INFORMATION: /note= "serine is linked to CH3C(O)
in formula (V A) or (V B)"

( i x ) FEATURE:
( A ) NAME/KEY: Peptide
( B ) LOCATION: 4
( D ) OTHER INFORMATION: /note= "DIQ-NH-tBu* is connected to
Phe via Psi[]in formula (V A) or (V B)"

( x i ) SEQUENCE DESCRIPTION: SEQ ID NO:5:

Ser Leu Asn Phe
1

( 2 ) INFORMATION FOR SEQ ID NO:6:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( v ) FRAGMENT TYPE: internal ( i x ) FEATURE:
( A ) NAME/KEY: Peptide
( B ) LOCATION: 1
( D ) OTHER INFORMATION: /note= "sequence = Y1 in formula
( I I I   A ) and (III B)"

( x i ) SEQUENCE DESCRIPTION: SEQ ID NO:6:

Ser Gln Asn Phe
1

( 2 ) INFORMATION FOR SEQ ID NO:7:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( v ) FRAGMENT TYPE: internal ( i x ) FEATURE:
( A ) NAME/KEY: Peptide
( B ) LOCATION: 1
( D ) OTHER INFORMATION: /note= "sequence = Y1 in formula
( I I I   A ) and (III B)"

( x i ) SEQUENCE DESCRIPTION: SEQ ID NO:7:

Ser  Ala  Ala  Phe
1

( 2 ) INFORMATION FOR SEQ ID NO:8:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: Peptide
        ( B ) LOCATION: 1
        ( D ) OTHER INFORMATION: /note= "sequence = Y1 in formula
        ( I I I   A ) and (III B)"

( x i ) SEQUENCE DESCRIPTION: SEQ ID NO:8:

Val  Ser  Glu  Asn
1

( 2 ) INFORMATION FOR SEQ ID NO:9:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: Peptide
        ( B ) LOCATION: 1
        ( D ) OTHER INFORMATION: /note= "sequence = Y1 in formula
        ( I I I   A ) and (III B)"

( x i ) SEQUENCE DESCRIPTION: SEQ ID NO:9:

Ser  Leu  Asn  Phe
1

( 2 ) INFORMATION FOR SEQ ID NO:10:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: Peptide
        ( B ) LOCATION: 1
        ( D ) OTHER INFORMATION: /note= "sequence = Y1 in formula
        ( I I I   A ) and (III B)"

( x i ) SEQUENCE DESCRIPTION: SEQ ID NO:10:

Val  Ser  Gln  Asn  Leu
1                      5

( 2 ) INFORMATION FOR SEQ ID NO:11:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
    ( A ) NAME/KEY: Peptide
    ( B ) LOCATION: 1
    ( D ) OTHER INFORMATION: /note= "sequence = Y1 in formula
    ( I I I  A ) and (III B)"

( x i ) SEQUENCE DESCRIPTION: SEQ ID NO:11:

Val  Ser  Gln  Asn  Phe
1                          5

( 2 ) INFORMATION FOR SEQ ID NO:12:

( i ) SEQUENCE CHARACTERISTICS:
    ( A ) LENGTH: 5 amino acids
    ( B ) TYPE: amino acid
    ( D ) TOPOLOGY: linear ( i i ) MOLECULE TYPE: peptide ( v ) FRAGMENT TYPE: internal ( i x ) FEATURE:
    ( A ) NAME/KEY: Peptide
    ( B ) LOCATION: 1
    ( D ) OTHER INFORMATION: /note= "sequence = Y1 informula
    ( I I I  A ) and (III B)"

( x i ) SEQUENCE DESCRIPTION: SEQ ID NO:12:

His  Pro  Phe  His  Val
1                          5

( 2 ) INFORMATION FOR SEQ ID NO:13:

( i ) SEQUENCE CHARACTERISTICS:
    ( A ) LENGTH: 4 amino acids
    ( B ) TYPE: amino acid
    ( D ) TOPOLOGY: linear ( i i ) MOLECULE TYPE: peptide ( v ) FRAGMENT TYPE: internal ( i x ) FEATURE:
    ( A ) NAME/KEY: Peptide
    ( B ) LOCATION: 1
    ( D ) OTHER INFORMATION: /note= "sequence = R"in formula
    ( V I  A )"

( x i ) SEQUENCE DESCRIPTION: SEQ ID NO:13:

Asn  Gln  Ser  Val
1

( 2 ) INFORMATION FOR SEQ ID NO:14:

( i ) SEQUENCE CHARACTERISTICS:
    ( A ) LENGTH: 4 amino acids
    ( B ) TYPE: amino acid
    ( D ) TOPOLOGY: linear ( i i ) MOLECULE TYPE: peptide ( v ) FRAGMENT TYPE: internal ( i x ) FEATURE:
    ( A ) NAME/KEY: Peptide
    ( B ) LOCATION: 1
    ( D ) OTHER INFORMATION: /note= "sequence = R"in formula
    ( V I  A )"

( x i ) SEQUENCE DESCRIPTION: SEQ ID NO:14:

His Phe Pro His
1

( 2 ) INFORMATION FOR SEQ ID NO:15:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: Peptide
        ( B ) LOCATION: 5
        ( D ) OTHER INFORMATION: /note= "Xaa = Nle"

( i x ) FEATURE:
        ( A ) NAME/KEY: Peptide
        ( B ) LOCATION: 6
        ( D ) OTHER INFORMATION: /note= "Phe is modified with p-NO2"

( i x ) FEATURE:
        ( A ) NAME/KEY: Peptide
        ( B ) LOCATION: 9
        ( D ) OTHER INFORMATION: /note= "Xaa = Nle having a terminal
              NH2"

( x i ) SEQUENCE DESCRIPTION: SEQ ID NO:15:

Lys Ala Arg Val Xaa Phe Glu Ala Xaa
1               5

( 2 ) INFORMATION FOR SEQ ID NO:16:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: Peptide
        ( B ) LOCATION: 1
        ( D ) OTHER INFORMATION: /note= "sequence = P1-Pn of formula
        ( V   A ) or (V B)"

( x i ) SEQUENCE DESCRIPTION: SEQ ID NO:16:

Tyr Asn Gln Ser Val
1               5

( 2 ) INFORMATION FOR SEQ ID NO:17:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: Peptide
        ( B ) LOCATION: 1
        ( D ) OTHER INFORMATION: /note= "sequence = P1-Pn of formula
        ( V   A ) or (V B)"

( x i ) SEQUENCE DESCRIPTION: SEQ ID NO:17:

```
Leu  Val  Arg  Ala  Lys
1                   5
```

( 2 ) INFORMATION FOR SEQ ID NO:18:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: Peptide
        ( B ) LOCATION: 1
        ( D ) OTHER INFORMATION: /note= "sequence = P1-Pn of formula
        ( V  A ) or (V B)"

( x i ) SEQUENCE DESCRIPTION: SEQ ID NO:18:

```
Met  Ile  Thr  Ala  Thr
1                   5
```

( 2 ) INFORMATION FOR SEQ ID NO:19:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: Peptide
        ( B ) LOCATION: 1
        ( D ) OTHER INFORMATION: /note= "sequence = P1-Pn of formula
        ( V  A ) or (V B)"

( x i ) SEQUENCE DESCRIPTION: SEQ ID NO:19:

```
Phe  Asn  Gly  Pro  Arg
1                   5
```

( 2 ) INFORMATION FOR SEQ ID NO:20:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: Peptide
        ( B ) LOCATION: 1
        ( D ) OTHER INFORMATION: /note= "sequence = P1-Pn of formula
        ( V  A ) or (V B)"

( x i ) SEQUENCE DESCRIPTION: SEQ ID NO:20:

```
Asn  Ala  Gln  Arg  Glu
1                   5
```

( 2 ) INFORMATION FOR SEQ ID NO:21:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
    ( A ) NAME/KEY: Peptide
    ( B ) LOCATION: 1
    ( D ) OTHER INFORMATION: /note= "sequence = P1-Pn of formula
    ( V A ) or (V B)"

( x i ) SEQUENCE DESCRIPTION: SEQ ID NO:21:

Phe Asn Phe Ser Val
1               5

( 2 ) INFORMATION FOR SEQ ID NO:22:

( i ) SEQUENCE CHARACTERISTICS:
    ( A ) LENGTH: 5 amino acids
    ( B ) TYPE: amino acid
    ( D ) TOPOLOGY: linear ( i i ) MOLECULE TYPE: peptide ( v ) FRAGMENT TYPE: internal ( i x ) FEATURE:
    ( A ) NAME/KEY: Peptide
    ( B ) LOCATION: 1
    ( D ) OTHER INFORMATION: /note= "sequence = P1-Pn of formula
    ( V A ) or (V B)"

( x i ) SEQUENCE DESCRIPTION: SEQ ID NO:22:

Phe Asn Leu Thr Cys
1               5

( 2 ) INFORMATION FOR SEQ ID NO:23:

( i ) SEQUENCE CHARACTERISTICS:
    ( A ) LENGTH: 5 amino acids
    ( B ) TYPE: amino acid
    ( D ) TOPOLOGY: linear ( i i ) MOLECULE TYPE: peptide ( v ) FRAGMENT TYPE: internal ( i x ) FEATURE:
    ( A ) NAME/KEY: Peptide
    ( B ) LOCATION: 1
    ( D ) OTHER INFORMATION: /note= "sequence = P1-Pn of formula
    ( V A ) or (V B)"

( x i ) SEQUENCE DESCRIPTION: SEQ ID NO:23:

Leu Ile Lys Arg Ile
1               5

( 2 ) INFORMATION FOR SEQ ID NO:24:

( i ) SEQUENCE CHARACTERISTICS:
    ( A ) LENGTH: 5 amino acids
    ( B ) TYPE: amino acid
    ( D ) TOPOLOGY: linear ( i i ) MOLECULE TYPE: peptide ( v ) FRAGMENT TYPE: internal ( i x ) FEATURE:
    ( A ) NAME/KEY: Peptide
    ( B ) LOCATION: 1
    ( D ) OTHER INFORMATION: /note= "sequence = P'1-P'm of
        formula (V A) or (V B)"

( x i ) SEQUENCE DESCRIPTION: SEQ ID NO:24:

Pro   Ile   Val   Gln   Asn
1                       5

( 2 ) INFORMATION FOR SEQ ID NO:25:

( i ) SEQUENCE CHARACTERISTICS:
    ( A ) LENGTH: 5 amino acids
    ( B ) TYPE: amino acid
    ( D ) TOPOLOGY: linear ( i i ) MOLECULE TYPE: peptide ( v ) FRAGMENT TYPE: internal ( i x ) FEATURE:
    ( A ) NAME/KEY: Peptide
    ( B ) LOCATION: 1
    ( D ) OTHER INFORMATION: /note= "sequence = P'1-P'm of
          formula (V A) or (V B)"

( x i ) SEQUENCE DESCRIPTION: SEQ ID NO:25:

Ala   Glu   Ala   Met   Ser
1                       5

( 2 ) INFORMATION FOR SEQ ID NO:26:

( i ) SEQUENCE CHARACTERISTICS:
    ( A ) LENGTH: 5 amino acids
    ( B ) TYPE: amino acid
    ( D ) TOPOLOGY: linear ( i i ) MOLECULE TYPE: peptide ( v ) FRAGMENT TYPE: internal ( i x ) FEATURE:
    ( A ) NAME/KEY: Peptide
    ( B ) LOCATION: 1
    ( D ) OTHER INFORMATION: /note= "sequence = P'1-P'm of
          formula (V A) or (V B)"

( x i ) SEQUENCE DESCRIPTION: SEQ ID NO:26:

Met   Gln   Arg   Gly   Asn
1                       5

( 2 ) INFORMATION FOR SEQ ID NO:27:

( i ) SEQUENCE CHARACTERISTICS:
    ( A ) LENGTH: 5 amino acids
    ( B ) TYPE: amino acid
    ( D ) TOPOLOGY: linear ( i i ) MOLECULE TYPE: peptide ( v ) FRAGMENT TYPE: internal ( i x ) FEATURE:
    ( A ) NAME/KEY: Peptide
    ( B ) LOCATION: 1
    ( D ) OTHER INFORMATION: /note= "sequence = P'1-P'm of
          formula (V A) or (V B)"

( x i ) SEQUENCE DESCRIPTION: SEQ ID NO:27:

Leu   Gln   Ser   Arg   Pro
1                       5

( 2 ) INFORMATION FOR SEQ ID NO:28:

( i ) SEQUENCE CHARACTERISTICS:
    ( A ) LENGTH: 5 amino acids
    ( B ) TYPE: amino acid

```
        ( D ) TOPOLOGY: linear ( i i ) MOLECULE TYPE: peptide ( v ) FRAGMENT TYPE: internal ( i x ) FEATURE:
        ( A ) NAME/KEY: Peptide
        ( B ) LOCATION: 1
        ( D ) OTHER INFORMATION: /note= "sequence = P'1-P'm of
              formula (V A) or (V B)"

( x i ) SEQUENCE DESCRIPTION: SEQ ID NO:28:

Phe  Gln  Ile  Thr  Leu
 1                   5

( 2 ) INFORMATION FOR SEQ ID NO:29:

( i ) SEQUENCE CHARACTERISTICS:
              ( A ) LENGTH: 5 amino acids
              ( B ) TYPE: amino acid
              ( D ) TOPOLOGY: linear ( i i ) MOLECULE TYPE: peptide ( v ) FRAGMENT TYPE: internal ( i x ) FEATURE:
              ( A ) NAME/KEY: Peptide
              ( B ) LOCATION: 1
              ( D ) OTHER INFORMATION: /note= "sequence = P'1-P'm of
                    formula (V A) or (V B)"

( x i ) SEQUENCE DESCRIPTION: SEQ ID NO:29:

Pro  Ile  Ser  Pro  Ile
 1                   5

( 2 ) INFORMATION FOR SEQ ID NO:30:

( i ) SEQUENCE CHARACTERISTICS:
              ( A ) LENGTH: 5 amino acids
              ( B ) TYPE: amino acid
              ( D ) TOPOLOGY: linear ( i i ) MOLECULE TYPE: peptide ( v ) FRAGMENT TYPE: internal ( i x ) FEATURE:
              ( A ) NAME/KEY: Peptide
              ( B ) LOCATION: 1
              ( D ) OTHER INFORMATION: /note= "sequence = P'1-P'm of
                    formula (V A) or (V B)"

( x i ) SEQUENCE DESCRIPTION: SEQ ID NO:30:

Phe  Leu  Asp  Gly  Ile
 1                   5
```